United States Patent
Li et al.

(10) Patent No.: US 8,674,136 B2
(45) Date of Patent: Mar. 18, 2014

(54) AROMATIC BUTAN-2-OL COMPOUNDS AND PREPARATION AND USES THEREOF

(75) Inventors: Song Li, Beijing (CN); Wu Zhong, Beijing (CN); Ping Liu, Beijing (CN); Junhai Xiao, Beijing (CN); Zhibing Zheng, Beijing (CN); Yunde Xie, Beijing (CN); Guoming Zhao, Beijing (CN); Xiaokui Wang, Beijing (CN); Lili Wang, Beijing (CN); Xingzhou Li, Beijing (CN); Xinbo Zhou, Beijing (CN)

(73) Assignee: Institute of Pharmacology and Toxicology Academy of Military Medical Sciences P.L.A. China (CN)

( * ) Notice: Subject to any disclaimer, the term of this patent is extended or adjusted under 35 U.S.C. 154(b) by 0 days.

(21) Appl. No.: 13/698,465

(22) PCT Filed: May 16, 2011

(86) PCT No.: PCT/CN2011/000849
§ 371 (c)(1),
(2), (4) Date: Dec. 14, 2012

(87) PCT Pub. No.: WO2011/143932
PCT Pub. Date: Nov. 24, 2011

(65) Prior Publication Data
US 2013/0085183 A1    Apr. 4, 2013

(30) Foreign Application Priority Data
May 17, 2010 (CN) .......................... 2010 1 0173785

(51) Int. Cl.
C07C 215/08 (2006.01)
C07C 215/30 (2006.01)
C07C 213/08 (2006.01)
A61K 31/045 (2006.01)
A61K 31/133 (2006.01)

(52) U.S. Cl.
USPC .......................................... 564/319; 514/648

(58) Field of Classification Search
None
See application file for complete search history.

(56) References Cited

FOREIGN PATENT DOCUMENTS

CN  1671667 A  9/2005
CN  1976704 A  6/2007

OTHER PUBLICATIONS

International Search Report mailed Aug. 25, 2011 (PCT/CN2011/000849); ISA/CN.
Liu, Ping et al. "(1R*,2R*)-1-(4-Chlorophenyl)-4-dimethylamino-1-(3-methoxy-2-naphthyl)-2-(1-naphthyl)butan-2-ol". Acta Cryst. Jun. 5, 2010, E66, pp. o1571 and sup-1-sup-9, especially pp. o1571, ISSN 1600-5368.
Liu, Ping et al. "(1R*,2R*)-1-(7-Bromo-3-methoxy-naphthalen-2-yl)-4-(dimethylamino)-2-(naphthalene-1-yl)-1-phenylbutan-2-ol". Acta Cryst. Feb. 13, 2010, E66, pp. o636 and sup-1-sup-9, especially pp. o636 and sup-1, ISSN 1600-5368.
Lucas, Simon et al. "Novel aldosterone synthase inhibitors with extended carbocyclic skeleton by a combined ligand-based and structure-based drug design approach". J. Med. Chem. 2008, vol. 51, No. 19, pp. 6138-6149, especially Scheme 2 in p. 6142.
Tran Huu-Anh et al. "O-Ethoxycarbonylmethoxy esters of homocalix[n]naphthalenes: synthesis and recognition behaviour towards alkali cations". J Incl Phenom Macrocycl Chem. 2008, vol. 60, pp. 43-49, especially Scheme 2 in p. 47.

Primary Examiner — Brian J Davis
(74) Attorney, Agent, or Firm — Banner & Witcoff, Ltd.

(57) ABSTRACT

Aromatic butan-2-ol compounds, preparation methods for making the compounds, and uses of the compounds are provided. Specifically, the compound of Formula I, or an optical isomer, racemate, diastereomer, pharmaceutically acceptable salt, or solvate thereof, is provided, where each of the substituents is defined. In addition, a pharmaceutical composition containing the compound, and the use of the compound in manufacture of a medicament for the treatment and/or prophylaxis of a disease or disorder caused by *tubercle bacillus* infection, is provided.

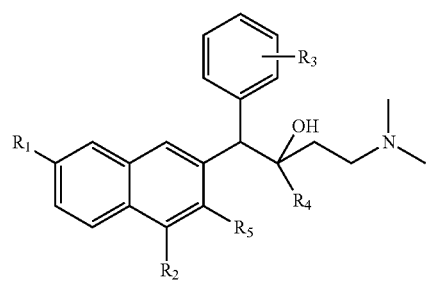

11 Claims, No Drawings

AROMATIC BUTAN-2-OL COMPOUNDS AND PREPARATION AND USES THEREOF

The present application is a U.S. National Phase filing of International Application No. PCT/CN2011/000849, filed on May 16, 2011, designating the United States of America and claiming priority to China Patent Application No. 201010173785.4, filed May 17, 2010. The present application claims priority to and the benefit of all the above-identified applications, and all the above-identified applications are incorporated by reference herein in their entireties.

TECHNICAL FIELD

The present invention relates to aromatic butan-2-ol compounds or optical isomers, racemates, diastereomers or pharmaceutically acceptable salts thereof. The present invention also relates to a process for preparing a compound of Formula I, a pharmaceutical composition comprising such compounds, and use of such compounds for combating *tubercle bacillus*.

BACKGROUND ART

Like AIDS, tuberculosis is another serious infectious disease threatening the world and causing the death of 2-3 millions of patients. In the world, there are about 11 millions patients infected with HIV and *tubercle bacillus* in combination. When AIDS is at onset in patients, due to hypoimmunity, the once dormant *tubercle bacillus* proliferate excessively, and with the increase of number of patients infected with HIV, the infection rate of tuberculosis increases again. However, there is no newly marketed drug in recent 40 years due to various reasons. Although the current antitubercular agents may inhibit the spreading of *tubercle bacillus* in some extent, they are not promising when drug resistant strains increase and cross drug resistant strains appear. In addition, the treatment cycle of current antitubercular agents in clinic use is usually more than 6 months, so that patients may not be compliant in such a long treatment period, and the number of drug resistant stains may increase continuously. Hence, it is necessary to develop antitubercular agents for quick treatment. In this connection, there is a need in the field to develop antitubercular agents with new structure and acting to new target point.

ATP synthetase is a new antitubercular target, and has a promising application prospect. The new aromatic butan-2-ol compounds are compounds against *tubercle bacillus* as designed for this target.

DISCLOSURES OF THE INVENTION

The object of the present invention is to discover and develop a new inhibitor of *tubercle bacillus* ATP synthetase, which is useful for treating or preventing tuberculosis, drug-resistant tuberculosis and multidrug-resistant tuberculosis by inhibiting *tubercle bacillus* ATP synthetase.

After conducting extensive research, the inventors have found that the novel aromatic butan-2-ol compounds of Formula I as provided in the present invention have an excellent effect against *tubercle bacillus*. Based on this finding, the present invention has been completed.

The first aspect of the present invention is to provide a compound of Formula I,

I 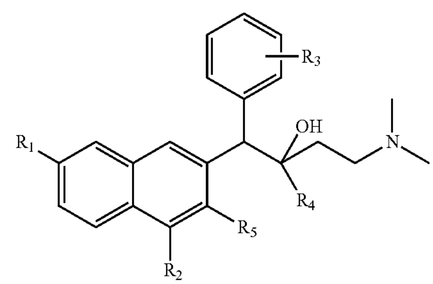 or an optical isomer, racemate, diastereomer, pharmaceutically acceptable salt or solvate thereof, wherein

- R1 represents hydrogen or a group selected from the group consisting of: fluoro, chloro, bromo, iodo, hydroxy, alkoxy, methoxy, nitro, amino and alkyl;
- R2 represents hydrogen, fluoro, chloro, bromo, iodo, alkyl, nitro or amino;
- R3 represents hydrogen or represents 1 to 5 (e.g., 1-4, 1-3 or 1-2) substituents independently selected from the group consisting of: fluoro, chloro, bromo, iodo, hydroxy, alkoxy, methoxy, nitro, amino and alkyl;
- R4 represents phenyl, naphthyl and a heterocyclic group, wherein the phenyl, naphthyl and heterocyclic group are optionally substituted with one or more (e.g., 1-5, 1-4, 1-3 or 1-2) substituents independently selected from the group consisting of: fluoro, chloro, bromo, iodo, hydroxy, alkoxy, methoxy, nitro, amino and alkyl; and
- R5 represents hydroxy, thiol, alkoxy, alkylthio or halogen.

In one embodiment of this aspect, the present invention provides a compound of Formula I, or an optical isomer, racemate, diastereomer, pharmaceutically acceptable salt or solvate thereof, wherein

- R1 represents hydrogen, fluoro, chloro, bromo, iodo or methoxy;
- R2 represents hydrogen, fluoro, chloro, bromo or iodo;
- R3 represents hydrogen, fluoro, chloro, bromo, iodo or C1-8 alkyl substituted at an o-, m- or p-position of the phenyl ring;
- R4 represents phenyl, substituted phenyl, or naphthyl; and
- R5 represents hydroxy, thiol, C1-8 alkoxy or methylthio.

In another embodiment of this aspect, the present invention provides a compound of Formula I, or an optical isomer, racemate, diastereomer, pharmaceutically acceptable salt or solvate thereof, wherein

- R1 represents hydrogen, fluoro, chloro, bromo or iodo;
- R3 represents hydrogen, fluoro, chloro, bromo, iodo or C1-6 alkyl substituted at an o-, m- or p-position of the phenyl ring;
- R4 represents phenyl, phenyl substituted with one or more halogens, or naphthyl; and
- R5 represents hydroxy or C1-6 alkoxy.

In another embodiment of this aspect, the present invention provides a compound of Formula I, or an optical isomer, racemate, diastereomer, pharmaceutically acceptable salt or solvate thereof, wherein

- R1 represents hydrogen, chloro or bromo;
- R2 represents hydrogen, chloro or bromo;
- R3 represents hydrogen, chloro, bromo or C1-4 alkyl substituted at an o-, m- or p-position of the phenyl ring;

R4 represents phenyl, 2-bromophenyl, 3-bromophenyl, 4-bromophenyl, 2,4-difluorophenyl, 3,5-difluorophenyl or naphthyl; and R5 represents hydroxy or C1-4 alkoxy.

In another embodiment of this aspect, the present invention provides a compound of Formula I, or an optical isomer, racemate, diastereomer, pharmaceutically acceptable salt or solvate thereof, wherein R1 represents hydrogen or bromo;

R2 represents hydrogen or bromo;

R3 represents hydrogen, chloro, bromo or methyl substituted at an o-, m- or p-position of the phenyl ring; and R5 represents hydroxy or methoxy.

In a specific embodiment of this aspect, the present invention provides a compound selected from the group consisting of:

(1) 1-phenyl-2-(1-naphthyl)-1-[2-(3-methoxy)naphthyl]-4-(N,N-dimethylamino)-butan-2-ol, (2) 1-(4-chlorophenyl)-2-(1-naphthyl)-1-[2-(7-bromo-3-methoxy)naphthyl]-4-(N,N-dimethylamino)-butan-2-ol, (3) 1-(4-chlorophenyl)-2-(1-naphthyl)-1-[2-(3-methoxy)naphthyl]-4-(N,N-dimethylamino)-butan-2-ol, (4) 1-(4-chlorophenyl)-2-(4-bromophenyl)-1-[2-(7-bromo-3-methoxy) naphthyl]-4-(N,N-dimethylamino)-butan-2-ol, (5) 1-phenyl-2-(4-bromophenyl)-1-[2-(7-bromo-3-methoxy)naphthyl]-4-(N,N-dimethylamino)-butan-2-ol, (6) 1-phenyl-2-(3-bromophenyl)-1-(2-[7-bromo-3-methoxy)naphthyl]-4-(N,N-dimethylamino)-butan-2-ol, (7) 1-(4-chlorophenyl)-2-(2,4-difluorophenyl)-1-[2-(3-methoxy)naphthyl]-4-(N,N-dimethylamino)-butan-2-ol, (8) 1-(4-chlorophenyl)-2-(3-bromophenyl)-1-[2-(7-bromo-3-methoxy) naphthyl]-4-(N,N-dimethylamino)-butan-2-ol, (9) 1-(4-chlorophenyl)-2-phenyl-1-(2-[7-bromo-3-methoxy)naphthyl]-4-(N,N-dimethylamino)-butan-2-ol,

(10) 1,2-diphenyl-1-[2-(7-bromo-3-methoxy)naphthyl]-4-(N,N-dimethylamino)-butan-2-ol,

(11) 1-(4-chlorophenyl)-2-(2-bromophenyl)-1-[2-(7-bromo-3-methoxy) naphthyl]-4-(N,N-dimethylamino)-butan-2-ol,

(12) 1-phenyl-2-(2-bromophenyl)-1-[2-(7-bromo-3-methoxy)naphthyl]-4-(N,N-dimethylamino)-butan-2-ol,

(13) 1-phenyl-2-(1-naphthyl)-1-[2-(7-bromo-3-methoxy) naphthyl]-4-(N,N-dimethylamino)-butan-2-ol,

(14) 1-(4-methylphenyl)-2-(1-naphthyl)-1-[2-(7-bromo-3-methoxy)naphthyl]-4-(N,N-dimethylamino)-butan-2-ol,

(15) 1-phenyl-2-(1-naphthyl)-1-[2-(4,7-dibromo-3-methoxy)naphthyl]-4-(N,N-dimethylamino)-butan-2-ol,

(16) 1,6-dibromo-3-[1-phenyl-2-(1-naphthyl)-2-hydroxy-4-(N,N-dimethylamino)]butyl-2-naphthol,

(17) 1-(3-chlorophenyl)-2-(1-naphthyl)-1-[2-(7-bromo-3-methoxy) naphthyl]-4-(N,N-dimethylamino)-butan-2-ol,

(18) 1-(3-methylphenyl)-2-(1-naphthyl)-1-[2-(7-bromo-3-methoxy) naphthyl]-4-(N,N-dimethylamino)-butan-2-ol,

(19) 1-(2-methylphenyl)-2-(1-naphthyl)-1-[2-(7-bromo-3-methoxy) naphthyl]-4-(N,N-dimethylamino)-butan-2-ol, and

(20) 1-(4-chlorophenyl)-2-(1-naphthyl)-1-[2-(3-methoxy) naphthyl]-4-(N,N-dimethylamino)-butan-2-ol hydrochloride, or their optical isomers, racemates, diastereomers, pharmaceutically acceptable salts or solvates.

In another embodiment of this aspect, the present invention relates to the optical isomers, racemates or diastereomers of the compounds.

In another embodiment of this aspect, the present invention relates to pharmaceutically acceptable salts of the compounds, including but not being limited to hydrochloride, hydrobromide, hydroiodide and sulfate.

The second aspect of the present invention provides a pharmaceutical composition comprising a compound of Formula I as defined above, or an optical isomer, racemate, diastereomer, pharmaceutically acceptable salt or solvate thereof, and optionally one or more pharmaceutically acceptable carriers or excipients.

In one embodiment of this aspect, the present invention provides a pharmaceutical composition comprising a compound of Formula I as defined above, or an optical isomer, racemate, diastereomer, pharmaceutically acceptable salt or solvate thereof; an additional agent useful for the treatment and/or prophylaxis of a disease or disorder caused by *tubercle bacillus* infection; and optionally one or more pharmaceutically acceptable carriers or excipients.

The third aspect of the present invention provides use of a compound of Formula I as defined above or an optical isomer, racemate, diastereomer, pharmaceutically acceptable salt or solvate thereof or the pharmaceutical composition of the present invention in manufacture of a medicament for the treatment and/or prophylaxis of a disease or disorder caused by *tubercle bacillus* infection. In one embodiment, the disease or disorder caused by *tubercle bacillus* infection is tuberculosis, such as pulmonary tuberculosis.

Alternatively, the present invention provides a method for the treatment and/or prophylaxis of a disease or disorder caused by *tubercle bacillus* infection in a subject in such need, the method comprises administering to the subject a therapeutically and/or prophylactically effective amount of a compound of Formula I as defined above or an optical isomer, racemate, diastereomer, pharmaceutically acceptable salt or solvate thereof or the pharmaceutical composition of the present invention. In one embodiment, the disease or disorder caused by *tubercle bacillus* infection is tuberculosis, such as pulmonary tuberculosis.

The fourth aspect of the present invention provides a compound of Formula I as defined above or an optical isomer, racemate, diastereomer, pharmaceutically acceptable salt or solvate thereof for the treatment and/or prophylaxis of a disease or disorder caused by *tubercle bacillus* infection. In one embodiment, the disease or disorder caused by *tubercle bacillus* infection is tuberculosis, such as pulmonary tuberculosis.

The terms and phrases used herein have general meanings well known by those skilled in the art. Nevertheless, it is intended to illustrate and explain some of the terms and phrases. Where the mentioned terms and phrases have meanings inconsistent with the well accepted meanings, the meanings as defined herein should prevail. The definitions of some terms used in the present invention are given below, and these definitions are applicable throughout the specification of the present application, unless specifically indicated otherwise in specific situations.

In the context of the present invention, for example, as described in general formula compounds or specific compounds, one atomic group may link to several hydrogen atoms, so that the atomic group may satisfy the requirements of chemical valence, even if hydrogen atoms on the corresponding atomic group are not shown in the structural formula.

When the term "alkyl" is mentioned alone, it may refer to any straight or branched alkyl having any number of carbon atoms, and especially to a straight or branched alkyl having 1-20 (e.g., 1-15, 1-10, 1-8, 1-6, 1-5, 1-4, 1-3 or 1-2) carbon atoms. In a specific embodiment, the term "alkyl" as mentioned alone in the present invention refers to a straight or branched alkyl having 1-8 (e.g., 1-6, 1-5, 1-4, 1-3 or 1-2) carbon atoms. For example, when "01-6 alkyl" is mentioned, it may further comprise a sub-scope of groups represented by C1-5 alkyl, C1-4 alkyl, C2-6 alkyl, C2-4 alkyl, etc., and specific groups such as methyl, ethyl, n-propyl, isopropyl, n-butyl, sec-butyl, tert-butyl, pentyl and hexyl.

The term "alkoxy" refers to alkyl-O—, wherein alkyl has the meaning as defined above.

As used herein, the term "halo", "halogen", "halogen atom", or "halogenated", etc., represents fluoro, chloro, bromo or iodo, and especially represents fluoro, chloro or bromo.

In the compound of Formula I of the present invention, when a substituent is depicted to the internal of a ring, it represents that the substituent may be substituted at any substitutable positions of the ring. For example, as for

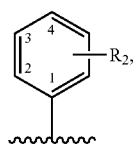

it represents one or more R2 substituents may be substituted at the 2-, 3-, 4-, 5- or 6-position of the ring.

As used herein, the term "effective amount" refers to a dose that may achieve the treatment and/or prophylaxis of the disease or disorder in a subject.

As used herein, the term "subject" refers to a patient or other animal, especially a mammal, such as human, dog, monkey, cattle, horse, etc., that is administered with the compound of Formula I of the present invention or a pharmaceutical composition thereof for the treatment and/or prophylaxis of the disease or disorder of the present invention.

As used herein, the term "disease and/or disorder" refers to a body status of the subject, and the body status relates to the disease and/or disorder.

As used herein, the percentage "%" refers to a weight/weight percentage, especially when it is used to describe a solid substance, unless it is specifically mentioned otherwise. However, when being used to describe a liquid substance, the percentage "%" may refer to a percentage of weight/volume (for situations in which a solid is dissolved in a liquid), or refer to a volume/volume percentage (for situations in which a liquid is dissolved in a liquid).

As used herein, the term "pharmaceutically acceptable", for example in the term "pharmaceutically acceptable salt", means that the salt is a synthetic substance which not only is physiologically acceptable for the subject, but also of a value for application in pharmaceutics. For example, a salt as an intermediate formed during a chiral resolution may be useful in obtaining a final product of the present invention, although the intermediate cannot be directly administered to the subject.

The fifth aspect of the present invention provides a process for preparing a compound of Formula I, or an optical isomer or pharmaceutically acceptable salt thereof, comprising subjecting a 4,7-substituted-3-hydroxy-2-naphthoic acid derivative of formula II,

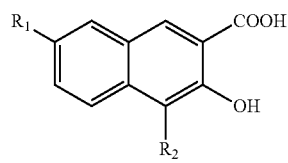

wherein R1 and R2 are as defined for the compound of Formula I in claim 1,
to methylation by dimethyl sulfate to obtain a compound of Formula III

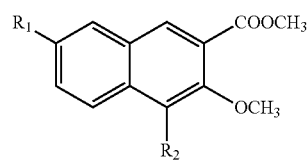

wherein R1 and R2 are as defined for the compound of Formula I in claim 1,
then subjecting to reduction by lithium aluminum hydride to obtain a compound of Formula IV

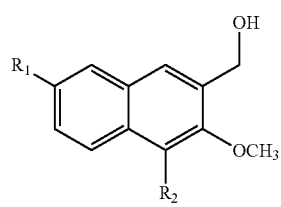

wherein R1 and R2 are as defined for the compound of Formula I in claim 1,
then subjecting to oxidation by manganese dioxide to obtain a compound of Formula V

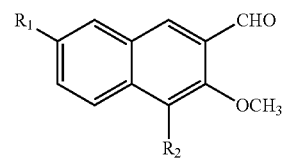

wherein R1 and R2 are as defined for the compound of Formula I in claim 1,
then subjecting to a reaction of nucleophilic addition with a substituted bromobenzene of Formula VI in the presence of magnesium turnings,

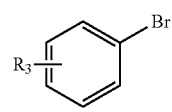

wherein R3 is as defined for the compound of Formula I in claim 1, to obtain a compound of Formula VII

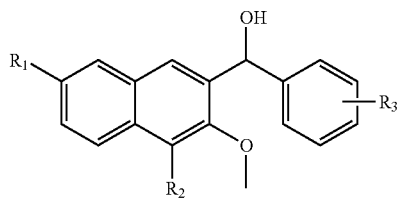

VII wherein R1, R2 and R3 are as defined for the compound of Formula I in claim 1, subjecting the compound of Formula VII to reduction by a mixture of aluminum trichloride and sodium borohydride to obtain a compound of Formula VIII

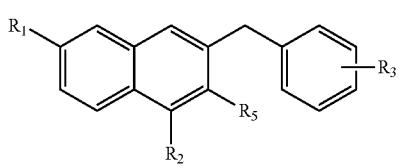

VIII wherein R1, R2, R3 and R5 are as defined for the compound of Formula I in claim 1, subjecting a substituted acetyl derivative of Formula IX

IX wherein R4 is as defined for the compound of Formula I in claim 1, to a Mannich reaction, then alkalization to obtain a compound of Formula X

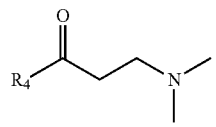

X wherein R4 is as defined for the compound of Formula I in claim 1, allowing a reaction of nucleophilic addition between the compound of Formula VIII and the compound of Formula X to obtain a compound of Formula I

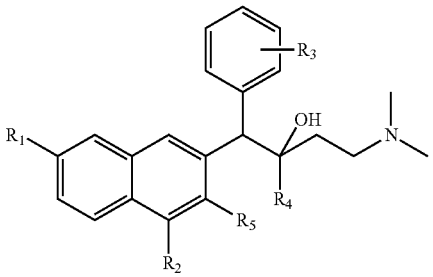

I wherein R1, R2, R3, R4 and R5 are as defined for the compound of Formula I in claim 1; and allowing the compound of Formula I to be a salt in the presence of an excessive acid to obtain a compound of Formula XI

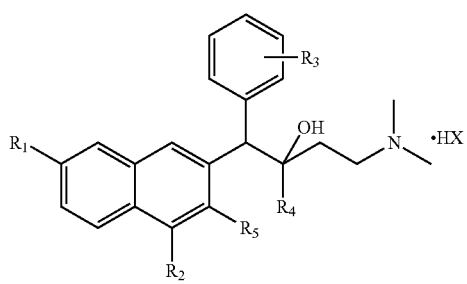

XI wherein R1, R2, R3, R4 and R5 are as defined for the compound of Formula I in the present invention, and HX is a pharmaceutically acceptable salt.

An exemplary synthesis scheme of the compound of the present invention is indicated as follows:

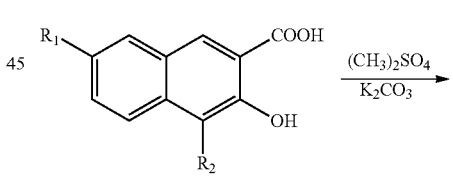

II

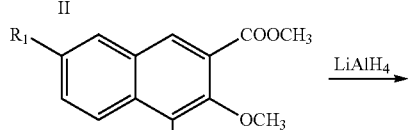

III

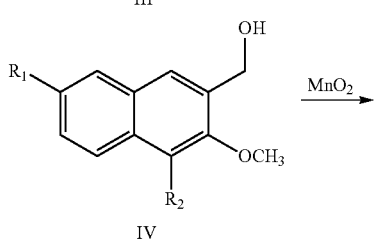

IV

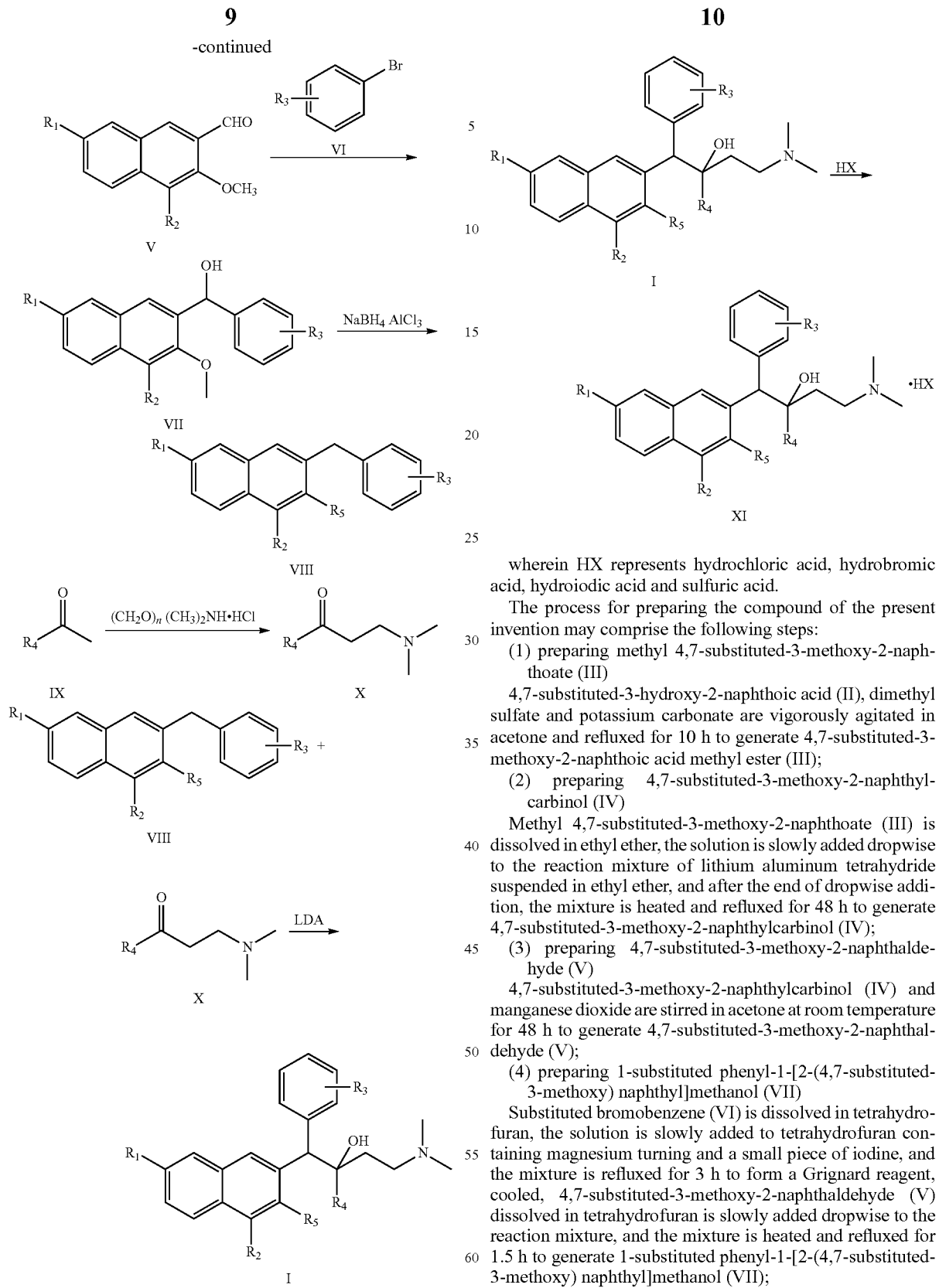

wherein HX represents hydrochloric acid, hydrobromic acid, hydroiodic acid and sulfuric acid.

The process for preparing the compound of the present invention may comprise the following steps:

(1) preparing methyl 4,7-substituted-3-methoxy-2-naphthoate (III)

4,7-substituted-3-hydroxy-2-naphthoic acid (II), dimethyl sulfate and potassium carbonate are vigorously agitated in acetone and refluxed for 10 h to generate 4,7-substituted-3-methoxy-2-naphthoic acid methyl ester (III);

(2) preparing 4,7-substituted-3-methoxy-2-naphthylcarbinol (IV)

Methyl 4,7-substituted-3-methoxy-2-naphthoate (III) is dissolved in ethyl ether, the solution is slowly added dropwise to the reaction mixture of lithium aluminum tetrahydride suspended in ethyl ether, and after the end of dropwise addition, the mixture is heated and refluxed for 48 h to generate 4,7-substituted-3-methoxy-2-naphthylcarbinol (IV);

(3) preparing 4,7-substituted-3-methoxy-2-naphthaldehyde (V)

4,7-substituted-3-methoxy-2-naphthylcarbinol (IV) and manganese dioxide are stirred in acetone at room temperature for 48 h to generate 4,7-substituted-3-methoxy-2-naphthaldehyde (V);

(4) preparing 1-substituted phenyl-1-[2-(4,7-substituted-3-methoxy) naphthyl]methanol (VII)

Substituted bromobenzene (VI) is dissolved in tetrahydrofuran, the solution is slowly added to tetrahydrofuran containing magnesium turning and a small piece of iodine, and the mixture is refluxed for 3 h to form a Grignard reagent, cooled, 4,7-substituted-3-methoxy-2-naphthaldehyde (V) dissolved in tetrahydrofuran is slowly added dropwise to the reaction mixture, and the mixture is heated and refluxed for 1.5 h to generate 1-substituted phenyl-1-[2-(4,7-substituted-3-methoxy) naphthyl]methanol (VII);

(5) preparing 1,6-substituted-2-substituted-3-substituted benzylnaphthalene (VIII)

1-substituted phenyl-1-[2-(4,7-substituted-3-methoxy) naphthyl]methanol (VII) and sodium borohydride are dissolved in tetrahydrofuran. The solution is added with anhydrous aluminum trichloride under an ice bath, stirred at a After the above synthetic procedures, the resulting compounds of the present invention are further subjected to the following reaction to yield salts of the compounds of the present invention:

temperature not more than 20° C. for 0.5 h, warmed and refluxed for 20 h to generate 1,6-substituted-2-substituted-3-substituted benzylnaphthalene (VIII);

(6) preparing 1-substituted-3-(N,N-dimethylamino)-1-acetone (X)

Substituted acetyl (IX), paraformaldehyde and dimethylamine hydrochloride are refluxed in 95% ethanol containing a small amount of concentrated hydrochloric acid for 2 h. The mixture is diluted with addition of acetone, and frozen to precipitate 1-substituted-3-(N,N-dimethylamino)-1-acetone (X) hydrochloride, which is then alkalified with sodium carbonate to obtain 1-substituted-3-(N,N-dimethylamino)-1-acetone (X);

(7) preparing the target compound 1-substituted phenyl-2-substituted-1-[2-(4,7-substituted-3-substituted)naphthyl]-4-(N,N-dimethylamino)-butan-2-ol (I)

Diisopropylamine is dissolved in tetrahydrofuran at −40° C., the solution is slowly added dropwise with n-butyl lithium to generate lithium diisopropylamide, cooled to −78° C., and 1,6-substituted-2-substituted-3-substituted benzylnaphthalene (VIII) dissolved in tetrahydrofuran is added to the reaction mixture. The mixture is stirred for 40 min, then added dropwise with 1-substituted-3-(N,N-dimethylamino)-1-acetone (X) dissolved in tetrahydrofuran, and reacted at −78° C. for 8 h to generate 1-substituted phenyl-2-substituted-1-[2-(4,7-substituted-3-substituted)naphthyl]-4-(N,N-dimethylamino)-butan-2-ol (1); and (8) preparing the target compound (XI)

1-substituted phenyl-2-substituted-1-[2-(4,7-substituted-3-substituted) naphthyl]-4-(N,N-dimethylamino)-butan-2-ol (I) reacts with an excessive amount of an acid at room temperature for 3 h to generate the target compound (XI).

The further details for the preparation of the compounds of Formula I are given in the following Examples.

The compounds of Formula I of the present invention or its pharmaceutically acceptable salt may be solely used, or used together with a pharmaceutically acceptable carrier or excipient in form of pharmaceutical composition, when it is used in form of pharmaceutical composition, an effective amount of the compound of Formula I of the present invention or its pharmaceutically acceptable salt or hydrate and one or more pharmaceutically acceptable carriers or diluents are combined to form a suitable administration form or dosage form, and this procedure comprises blending, granulating, compressing or dissolving components via suitable manners. Hence, the present invention provides a pharmaceutical composition, which comprises a compound of Formula I as defined above, or all possible optical isomers, racemates, diastereomers or pharmaceutically acceptable salts or solvates or hydrates thereof and at least one pharmaceutically acceptable carrier.

The pharmaceutical composition of the present invention may be administered in any of the following manners: oral administration, spray inhalation, rectal administration, nasal administration, vaginal administration, local administration, parenteral administration, such as subcutaneous, intravenous, intramuscular, intraperitoneal, intrathecal, intraventricular, intrasternal, intracranial injection or perfusion, or administration with aid of an explanted reservoir, preferably oral administration, intramuscular, intraperitoneal or intravenous administration.

The compound of the present invention or a pharmaceutical composition containing the same may be administered in a unit dosage form. The dosage form may be liquid dosage form, or solid dosage form. The liquid dosage form may be true solutions, colloids, fine granules, emulsions, suspensions, other dosage forms such as tablets, capsules, drop pills, aerosols, pills, powders, solutions, suspensions, emulsions, granules, suppositories, lyophilized powder injections, inclusion complexes, implants, patches, and embrocations, etc.

The pharmaceutical composition of the present invention may further comprise conventional carriers, in which the pharmaceutically acceptable carriers include but are not limited to: ion exchangers, alumina, aluminum stearate, lecithin, serum protein such as human albumin, buffering substance such as phosphate, glycerol, sorbic acid, potassium sorbate, mixture of partial glycerides of saturated plant fatty acids, water, salts or electrolytes, such as protamine sulfate, disodium hydrogen phosphate, potassium hydrogen phosphate, sodium chloride, zinc salt, colloid silica, magnesium trisilicate, polyvinylpyrrolidone, cellulose substances, polyethylene glycol, sodium carboxymethylcellulose, polyacrylates, beeswax, or lanolin. The amount of carriers in the pharmaceutical composition may be 1 wt % to 98 wt %, usually about 80 wt %. For convenience, a local anesthetic, preservative, and buffering agent may be directly dissolved in the carrier.

Oral tablets and capsules may comprise excipients such as binding agents, such as syrup, Arabic gum, sorbitol, tragacanth gum, or polyvinylpyrrolidone, fillers such as lactose, sucrose, maize starch, calcium phosphate, sorbitol, or amino acids, lubricants such as magnesium stearate, talc, polyethylene glycol, silica, disintegrants such as potato starch, or acceptable wetting agent such as sodium laurinol sulfate. The tablets may be coated according to well-known methods in pharmaceutics.

Oral liquids may be formulated into suspensions of water and oil, solutions, emulsions, syrups or elixirs, or may also be processed in dry products which may be supplied with water or other suitable medium before use. This kind of liquid preparation may comprise conventional additives such as suspending agents, sorbitol, methyl cellulose, syrup of glucose, gels, hydroxyethylcellulose, carboxymethylcellulose, aluminum stearate gel, hydrogenated edible oil and fat, emulsifying agents, such as lecithin, sorbitan monooleate, Arabic gum; or non-aqueous carriers, such as almond oil, greases such as glycerol, ethylene glycol, or ethanol; preservatives such as methyl or propyl p-hydroxybenzoate, or sorbic acid. If necessary, flavoring agents or coloring agents may be added.

Suppositories may comprise a conventional suppository base, such as cocoa butter or other glycerides.

As for parenteral administration, liquid dosage forms are usually made of the compound and a sterilized carrier. The carrier is preferably water. According to the selected carrier and drug concentration, the compound may either be dissolved in the carrier or be processed in the form of a suspension solution, and when an injection solution is prepared, the compound is firstly dissolved in water, filtered, sterilized, and packaged in sealed bottles or ampoules.

It should be realized that the optimized dose and interval for administering the compound of Formula I depend on the properties of the compound and external conditions such as administration manner, route and site, and specific mammal to be treated, and this optimized dose may be determined using conventional technology. It also must be realized that the optimized treatment course, i.e., the daily dose of the compound of Formula I in a specified time period may be determined by well-known methods in the art.

The compounds of Formula I of the present invention may further comprise its isomers, racemates, enantiomers, diastereomers, enantiomer-enriching substances, solvates, and esters; the compound of Formula I and its isomers, racemates, enantiomers, diastereomers, enantiomer-enriching substances, solvates and esters may further form solvates, such as hydrates, or alcoholates. The above compound may further be prodrug or in a form that may release the active component after metabolism in vivo. It is well-known technique for those skilled in the art to select and prepare suitable prodrug derivatives. In general, in view of the purpose of the present invention, the solvates formed with pharmaceutically acceptable solvents, such as water and ethanol, are equivalent to the form of non-solvates.

The actual dosage levels of various active components in the pharmaceutical composition of the present invention are selected so that the resultant active compound amount may achieve the desired therapeutical effects for specific patients, compositions and administration manners. The dosage level must be selected according to the activity of specific compound, administration route, severity of disease and patient's conditions and medical history. However, the method in the art is that the dose of compound starts from a level lower than the requested level for achieving the desired therapeutical effects, then the dose gradually increases until the desired effects are achieved.

In general, the dose of the compound of Formula I of the present invention used to a mammal, especially a human, may be 0.001-1000 mg/kg body weight/day, for example, 0.01-100 mg/kg body weight/day, for example, 0.01-10 mg/kg body weight/day. For example, according to different administration manners, the composition may comprise 0.1%, more suitably 10-60% of active components in weight proportion. When the composition is of unit dose, each unit dose preferably comprises 50-500 mg of active component. For example, in one embodiment, according to administration route and frequency, a suitable therapeutic dose for an adult is 100-3000 mg, for example 1500 mg, per day. This dose corresponds to 1.5-50 mg/kg/day, or a suitable dose is 5-20 mg/kg/day.

The inventors have demonstrated by experiments that the compounds of Formula I as provided by the present invention have an activity effective against *tubercle bacillus*, and thus may be used for the treatment of various diseases or conditions caused by *tubercle bacillus*, for example, tuberculosis, such as pulmonary tuberculosis.

SPECIFIC MODES FOR CARRYING OUT THE INVENTION

The present invention is further described by the following examples, but the scope of the present invention is not limited to the examples. Those skilled in the art should appreciate that the present invention may be subjected to various changes and modifications without departing from the spirit and scope of the present invention.

The present invention provides general and/or specific descriptions for the used materials and experimental methods in the experiments. Although many materials and procedures used to achieve the purpose of the present invention are known in the art, they are described in detail as much as possible in the following examples.

The melting points of compounds are measured by a RY-1 melting point instrument, and thermometers are not calibrated. Mass spectra are measured by a Micromass ZabSpec high resolution mass spectrometer (resolution: 1000). 1H NMR is measured by a JNM-ECA-400 superconducting NMR meter, working frequency: 1H NMR 400 MHz.

EXAMPLE 1

Preparation of 4,7-dibromo-3-hydroxy-2-naphthoic acid

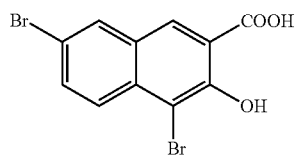 [SMILES: O=C(O)c1cc2cc(Br)ccc2c(Br)c1O]

In a 1 L three-necked bottle, 50 g of 3-hydroxy-2-naphthoic acid (0.27 mol) and 600 ml of glacial acetic acid were added, and the mixture was stirred to form a solution. 34 ml of bromine element (0.67 mol) was diluted with 100 ml of glacial acetic acid, slowly added dropwise to the reaction mixture, and the temperature was kept at 20-30° C. After the end of dropwise addition, the temperature was elevated to 125° C., and refluxed for 10 h. The heating was stopped, and the mixture was stirred, and slowly cooled to room temperature to precipitate a large amount of a solid. The solid was filtered off, and the filter cake was washed with water (200 ml*2), and dried in an oven to obtain 82.75 g of the solid with a yield of 90%.

EXAMPLE 2

Preparation of 7-bromo-3-hydroxy-2-naphthoic acid

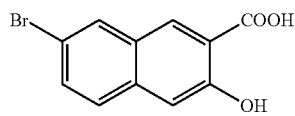 [SMILES: O=C(O)c1cc2cc(Br)ccc2cc1O]

In a 1 L three-necked bottle, 40 g of 4,7-dibromo-3-hydroxy-2-naphthoic acid (0.116 mol) and 500 ml of glacial acetic acid were added, and stirred to make homogenous. 18 g of tin powder (0.153 mol) and 130 ml of concentrated hydrochloric acid were then added to the mixture in order, heated to 125° C., and refluxed under heating for 12 h. 300 ml of water was added to the mixture, stirred to room temperature, filtered, and the filter cake was washed with water (200 ml*2), and dried in an oven to obtain 29.9 g of a solid with a yield of 96.5%.

EXAMPLE 3

Preparation of 7-bromo-3-methoxy-2-naphthoic acid methyl ester

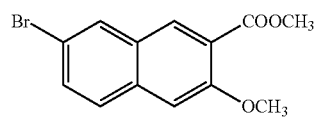

In a 250 ml three-necked bottle, 4.54 g of 7-bromo-3-hydroxy-2-naphthoic acid (0.017 mol), 11.69 g of potassium carbonate (0.085 mol) and 70 ml of acetone were added, and stirred to make homogenous. 2.3 ml of methyl iodide was added to the mixture, agitated vigorously, heated to 60° C., and refluxed for 10 h. After cooling to room temperature, and vacuum evaporating in rotational manner to remove acetone, 100 ml of water was added to the mixture, extracted with ethyl acetate (100 ml*3), and the organic layers were combined. The resultant organic layer was washed with water (30 ml*2) and saturated saline (20 ml*2), and dried over anhydrous magnesium sulfate for 3 h. The magnesium sulfate was removed by filtering, and the filtrate was dried under vacuum in a rotational manner to obtain a crude product which was subjected to a column chromatography (developing agent: ethyl acetate/petroleum ether=1/10) to obtain a product of 4.29 g with a yield of 86%.

EXAMPLE 4

Preparation of 7-bromo-3-methoxy-2-naphthylcarbinol

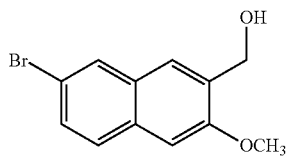

Under protection of nitrogen gas, in 1.5 L of three-necked bottle, 16 g of lithium aluminum hydride (0.421 mol) and 200 ml of anhydrous ethyl ether were added, and the mixture was stirred at room temperature for 20 min. 116.2 g of 7-bromo-3-methoxy-2-naphthylmethyl ester (0.395 mol) dissolved in 1 L of anhydrous ethyl ether was slowly added dropwise to the reaction mixture, and the reaction was kept under a slight boiling state. After completion of the addition, the mixture was refluxed under heating for 48 h to complete the reaction. The mixture was cooled to room temperature, 200 ml of water were slowly added dropwise to terminate the reaction, after separating out the ethyl ether layer, extracted with ethyl ether (200 ml*2), and the organic layers were combined. The organic layer was washed with water (300 ml*2) and saturated saline (200 ml*2), and dried over anhydrous magnesium sulfate for 3 h. The magnesium sulfate was removed by filtering, and the filtrate was dried under vacuum in a rotary dryer to obtain a relatively pure crude product of 104.9 g, which could be directly used in the next step.

EXAMPLE 5

Preparation of 7-bromo-3-methoxy-2-naphthaldehyde

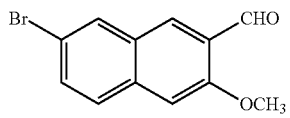 [SMILES: COc1cc2ccc(Br)cc2cc1C=O]

In a 500 ml three-necked bottle, 34.1 g of 7-bromo-3-methoxy-2-naphthylcarbinol (0.128 mol) and 350 ml of acetone were added, and the mixture was stirred vigorously to form a solution. 167 g of active manganese dioxide (1.92 mol) was added to the solution, and the mixture was stirred at room temperature for 48 h to complete the reaction. The mixture was filtered, and the manganese dioxide filter cake was washed with ethyl acetate (200 ml*6). The filtrates were combined, and dried under vacuum in a rotary dryer to obtain a crude product as a yellow solid, which was recrystallized from methanol to obtain 29.3 g with a yield of the two steps of 86%.

EXAMPLE 6

Preparation of 1-phenyl-1-[2-(7-bromo-3-methoxy) naphthyl]-methanol

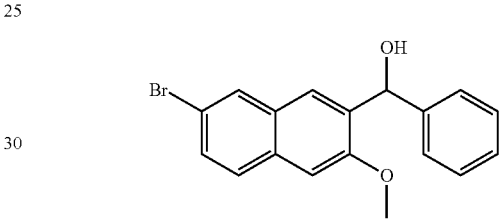

Under protection of nitrogen gas, in a 500 ml three-necked bottle, 6 g of magnesium turning (0.25 mol) and 50 ml of anhydrous tetrahydrofuran were added, and a small piece of iodine was added. 26.3 ml of bromobenzene (0.25 mol) and 40 ml of anhydrous tetrahydrofuran were mixed to form a homogeneous mixture, 10 ml of which mixture was added in one batch to the reaction mixture. The resulting mixture was slightly heated without stirring to generate gas bobbles, the heating was stopped, and the color of iodine disappeared gradually. When the reaction was not vigorous, the rest of the bromobenzene tetrahydrofuran solution was added dropwise under stirring, and the reaction mixture was kept slightly boiling. After completion of the addition, the mixture was refluxed under heating for 3 h. The reaction mixture was naturally cooled to room temperature, 26.4 g of 7-bromo-3-methoxy-2-naphthaldehyde (0.1 mol) mixed with 150 ml of anhydrous tetrahydrofuran were slowly added dropwise, and continuously refluxed under heating for 1.5 h. The reaction was cooled, and terminated by adding dropwise 50 ml of 5% diluted hydrochloric acid. The mixture was subjected to rotary evaporation under vacuum to remove tetrahydrofuran, extracted with ethyl acetate (100 ml*3), and all organic layers were combined. The organic layer was washed with saturated sodium carbonate solution (50 ml*2), washed with water (50 ml*2), washed with saturate saline (50 ml*2), and dried over anhydrous magnesium sulfate for 3 h. The magnesium sulfate was removed by filtering, and the filtrate was dried under vacuum in a rotary dryer to obtain a crude product of 36 g, which was directly used in the next step.

EXAMPLE 7

Preparation of 6-bromo-2-methoxy-3-benzylnaphthalene

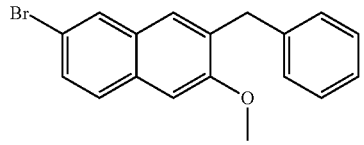 [SMILES: COc1cc2ccc(Br)cc2cc1Cc1ccccc1]

Under protection of nitrogen gas, in a 500 ml three-necked bottle, 36 g of 1-phenyl-1-[2-(7-bromo-3-methoxy)naphthyl]methanol (0.1 mol) and 200 ml of anhydrous tetrahydrofuran were added, and the mixture was stirred to be a solution. 20 g of sodium borohydride (0.5 mol) was then added to the solution, stirred in an ice-bath for 1 h, and 42 g of aluminum trichloride (0.3 mol) was added in batches, so that the reaction temperature was not greater than 20° C. After completion of the addition, the mixture was continuously stirred in an ice-bath for 20 min, and refluxed under heating for 20 h. The mixture was added with 50 ml of water to terminate the reaction, subjected to rotary evaporation under a reduced pressure to remove tetrahydrofuran, extracted with ethyl acetate (100 ml*3), and organic layers were combined. The resultant organic layer was washed with 5% hydrochloric acid (50 ml*2), saturated sodium carbonate solution (50 ml*2), water (50 ml*2), and saturated saline (50 ml*2), and dried over anhydrous magnesium sulfate for 3 h. The magnesium sulfate was removed by filtering, and the filtrate was dried under vacuum in a rotary dryer to obtain a crude product which was subjected to a column chromatography (developing agent: petroleum ether) to obtain a product of 25.5 g with a yield of the two steps of 78%.

EXAMPLE 8

Preparation of 1-(α-naphthyl)-3-(N,N-dimethylamino)-1-acetone

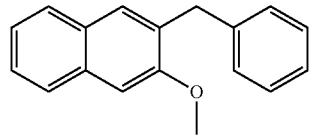 [SMILES: COc1cc2ccccc2cc1Cc1ccccc1]

In a 500 ml round bottomed flask, 85 g of 1-acetylnaphthalene (0.5 mol), 52.7 g of dimethylamine hydrochloride (0.65 mol) and 19.8 g of paraformaldehyde (0.22 mol) were added. 1 ml of concentrated hydrochloride acid and 80 ml of 95% ethanol were mixed to be dissolved, and the solution was poured into the flask, stirred, and refluxed under heating for 2 h. 400 ml of acetone was poured into the flask while it was warm, and the mixture was slowly cooled to room temperature, placed in refrigerator and frozen overnight to precipitate a solid which was filtered, and washed with acetone (50 ml*2) to obtain 1-(α-naphthyl)-3-(N,N-dimethylamino)-1-acetone hydrochloride. This salt was dissolved in water, and the solution was adjusted with sodium carbonate aqueous solution to have a basic pH, and extracted with ethyl acetate (100 ml*3). All organic layers were combined, washed with saturated sodium carbonate solution (50 ml*2), water (50 ml*2), and saturated saline (50 ml*2), and dried over anhydrous magnesium sulfate for 3 h. The magnesium sulfate was removed by filtering, and the filtrate was dried under vacuum in a rotary dryer to obtain a crude product of 81.7 g, which was directly used in the next step.

EXAMPLE 9

Preparation of 2-benzyl-3-methoxynaphthalene

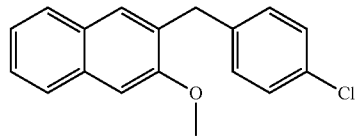 [SMILES: COc1cc2ccccc2cc1Cc1ccc(Cl)cc1]

Using 3-hydroxy-2-naphthoic acid as the starting material, the procedures of Examples 3-7 were repeated to obtain the compound 2-benzyl-3-methoxynaphthalene.

EXAMPLE 10

Preparation of 2-(4-chlorobenzyl)-3-methoxynaphthalene

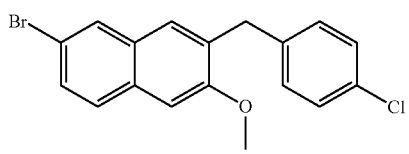 [SMILES: COc1cc2ccc(Br)cc2cc1Cc1ccc(Cl)cc1]

Using 3-hydroxy-2-naphthoic acid as the starting material, and 4-chlorobromobenzene to replace bromobenzene, the procedures of Examples 3-7 were repeated to obtain the compound 2-(4-chlorobenzyl)-3-methoxynaphthalene.

EXAMPLE 11

Preparation of 6-bromo-2-methoxy-3-(4-chlorobenzyl)-naphthalene

Using 4-chlorobromobenzene to replace bromobenzene, the procedures of Examples 6-7 were repeated to obtain the compound 6-bromo-2-methoxy-3-(4-chlorobenzyl)naphthalene.

EXAMPLE 12

Preparation of 1-(2-bromophenyl)-3-(N,N-dimethylamino)-1-acetone

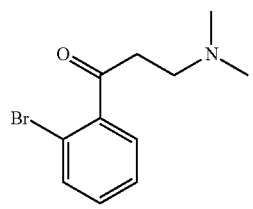

Using 2-bromoacetophenone to replace 1-acetylnaphthalene, the procedures of Example 8 were repeated to obtain the compound 1-(2-bromophenyl)-3-(N,N-dimethylamino)-1-acetone.

EXAMPLE 13

Preparation of 1-(3-bromophenyl)-3-(N,N-dimethylamino)-1-acetone

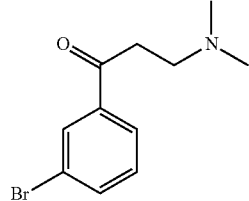

Using 3-bromoacetophenone to replace 1-acetylnaphthalene, the procedures of Example 8 were repeated to obtain the compound 1-(3-bromophenyl)-3-(N,N-dimethylamino)-1-acetone.

EXAMPLE 14

Preparation of 1-(4-bromophenyl)-3-(N,N-dimethylamino)-1-acetone

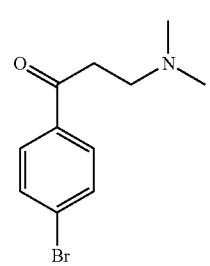

Using 4-bromoacetophenone to replace 1-acetylnaphthalene, the procedures of Example 8 were repeated to obtain the compound 1-(4-bromophenyl)-3-(N,N-dimethylamino)-1-acetone.

EXAMPLE 15

Preparation of 1-phenyl-3-(N,N-dimethylamino)-1-acetone

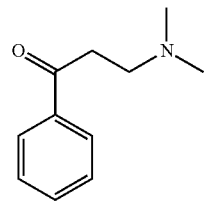

Using acetophenone to replace 1-acetylnaphthalene, the procedures of Example 8 were repeated to obtain the compound 1-phenyl-3-(N,N-dimethylamino)-1-acetone.

EXAMPLE 16

Preparation of 1-(2,4-difluorophenyl)-3-(N,N-dimethylamino)-1-acetone

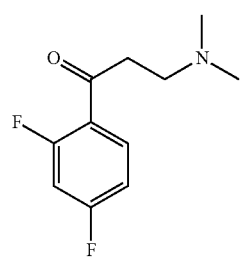

Using 2,4-difluoroacetophenone to replace 1-acetylnaphthalene, the procedures of Example 8 were repeated to obtain the compound 1-(2,4-difluorophenyl)-3-(N,N-dimethylamino)-1-acetone.

EXAMPLE 17

Preparation of 1-phenyl-2-(1-naphthyl)-1-[2-(3-methoxy)-naphthyl]-4-(N,N-dimethylamino)-butan-2-ol

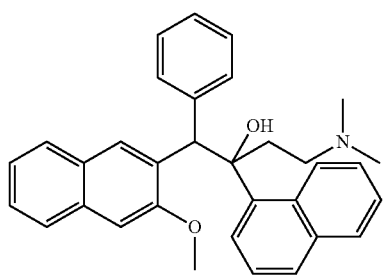 [SMILES: COc1cc2ccccc2cc1C(c1ccccc1)C(O)(CCN(C)C)c1cccc2ccccc12]

Compound 1 (A mesomer)
Compound 2 (B mesomer)

Under protection of nitrogen gas, in a 250 ml three-necked bottle, 2.8 ml of diisopropylamine (0.02 mol) and 20 ml of anhydrous tetrahydrofuran were added, and the mixture was stirred at −40° C. for 0.5 h. 8 ml of 2.5M n-butyl lithium (0.02 mol) was added to the reaction mixture dropwise using a syringe, and continuously stirred at −40° C. for 0.5 h. The reaction mixture was cooled to −78° C., and 2.46 g of 2-benzyl-3-methoxynaphthalene (0.01 mol) dissolved in 20 ml of anhydrous tetrahydrofuran was slowly added dropwise. After completion of the addition, the reaction was continuously stirred at −78° C. for 40 min. 3.9 g of in situ prepared 1-(α-naphthyl)-3-(N,N-dimethylamino)-1-acetone (0.017 mol) dissolved in 20 ml of anhydrous tetrahydrofuran was slowly added dropwise over 1 h to the reaction mixture, and after completion of the addition, stirred at −78° C. for 8 h. The reaction was heated to −40° C., 20 ml of saturated ammonium chloride aqueous solution for hydrolysis for 0.5 h was added, heated to room temperature, subjected to rotary evaporation under a reduced pressure to remove tetrahydrofuran, 50 ml of water was added, extracted with ethyl acetate (50 ml*3), and all organic layers were combined. The resultant organic layer was washed with water (30 ml*2), saturated saline (20 ml*2), and dried over anhydrous magnesium sulfate for 3 h. The magnesium sulfate was removed by filtering, and the filtrate was dried under vacuum in a rotary dryer to obtain a crude product which was subjected to a column chromatography (developing agent: dichloromethane/methanol/aqueous ammonia=400/1/0.1) to obtain two components sequentially, which were separately recrystallized from isopropyl ether to obtain Compound 1 (mp: 154.0-154.8° C.) and Compound 2 (mp: 185.7-187.7° C.).

Compound 1: 1H-NMR (400 MHz, CDCl3) δ=1.563 (s, 1H); 1.979 (m, 7H); 2.267 (m, 1H); 2,460 (m, 1H); 4.068 (s, 3H); 6.067 (s, 1H); 6.881 (m, 3H); 7.102 (s, 2H); 7.202 (s, 1H); 7.341 (m, 2H); 7.427 (t, J=7.2 Hz, 1H); 7.497 (t, J=7.2 Hz, 1H); 7.608 (m, 1H); 7.688 (d, J=7.6 Hz, 1H); 7.750 (d, J=8.0 Hz, 1H); 7.891 (m, 3H); 8.372 (s, 1H); 8.668 (d, J=8.0 Hz, 1H); 8.853 (s, 1H).

ESI MS: m/z=476.4 [M++1]

Compound 2: 1H-NMR (400 MHz, CDCl3) δ=1.565 (s, 1H); 1.989 (s, 7H); 2.358 (m, 1H); 2,497 (m, 1H); 3.022 (s, 3H); 5.886 (s, 1H); 6.531 (s, 1H); 7.213 (m, 5H); 7.387 (m, 4H); 7.536 (m, 2H); 7.712 (d, J=7.6 Hz, 1H); 7.777 (d, J=8.0 Hz, 1H); 7.937 (d, J=7.6 Hz, 2H); 7.976 (d, J=6.4 Hz, 1H); 8.193 (s, 1H); 8.394 (s, 1H); 8.540 (d, J=8.4 Hz, 1H).

ESI MS: m/z=476.3 [M++1]

EXAMPLE 18

Preparation of 1-(4-chlorophenyl)-2-(1-naphthyl)-1-[2-(7-bromo-3-methoxy)naphthyl]-4-(N,N-dimethylamino)-butan-2-ol

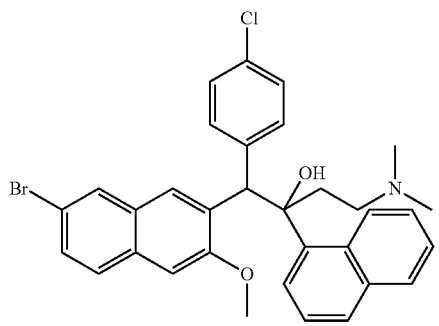 [SMILES: COc1cc2ccc(Br)cc2cc1C(c1ccc(Cl)cc1)C(O)(CCN(C)C)c1cccc2ccccc12]

Compound 3 (A mesomer)
Compound 4 (B mesomer)

Using 6-bromo-2-methoxy-3-(4-chlorobenzyl)naphthalene to replace 2-benzyl-3-methoxynaphthalene, the procedures of Example 12 were repeated to obtain Compound 3 (mp: 185.1-185.5° C.) and Compound 4 (mp: 149.0-149.9° C.).

Compound 3: 1H-NMR (400 MHz, DMSO-d6) δ=1.884 (m, 9H); 2.154 (m, 1H); 3.280 (s, 3H); 5.821 (s, 1H); 6.787 (s, 1H); 7.372 (m, 6H); 7.581 (m, 2H); 7.810 (m, 4H); 7.915 (d, J=1.6 Hz, 1H); 8.098 (d, J=7.6 Hz, 1H); 8.475 (s, 1H); 8.570 (d, J=9.2 Hz, 1H).

ESI MS: m/z=590.3 [M++1]

Compound 4: 1H-NMR (400 MHz, CDCl3) δ=1.601 (s, 1H); 1.964 (m, 7H); 2.174 (m, 1H); 2.451 (s, 1H); 4.069 (s, 3H); 6.008 (s, 1H); 6.838 (d, J=8.4 Hz, 2H); 7.063 (d, J=8.4 Hz, 2H); 7.164 (s, 1H); 7.346 (t, J=8.0 Hz, 2H); 7.491 (m, 2H); 7.601 (m, 2H); 7.694 (d, J=7.6 Hz, 2H); 7.904 (m, 2H); 8.021 (s, 1H); 8.387 (s, 1H); 8.594 (d, J=8.4 Hz, 1H); 8.667 (s, 1H).

ESI MS: m/z=590.3 [M++1]

EXAMPLE 19

Preparation of 1-(4-chlorophenyl)-2-(1-naphthyl)-1-[2-(3-methoxy)naphthyl]-4-(N,N-dimethylamino)-butan-2-ol (Compounds 5 and 6)

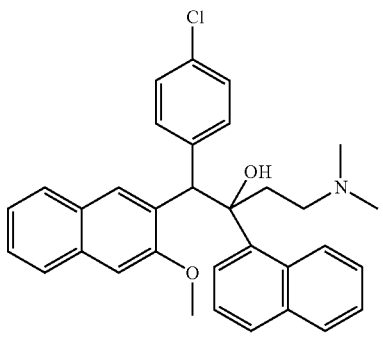 [SMILES: COc1cc2ccccc2cc1C(c1ccc(Cl)cc1)C(O)(CCN(C)C)c1cccc2ccccc12]

Compound 5 (A mesomer)
Compound 6 (B mesomer)

Using 3-methoxy-2-(4-chlorobenzyl)naphthalene to replace 2-benzyl-3-methoxynaphthalene, the procedures of Example 12 were repeated to obtain Compound 5 (mp: 215.4-215.9° C.) and Compound 6 (mp: 180.5-181.2° C.).

Compound 5: 1H-NMR (400 MHz, CDCl3) δ=2.004 (s, 8H); 2.272 (m, 1H); 2.480 (m, 1H); 3.092 (s, 3H); 5.848 (s, 1H); 6.544 (s, 1H); 7.209 (m, 3H); 7.318 (d, J=8.0 Hz, 2H); 7.397 (m, 2H); 7.526 (m, 2H); 7.694 (d, J=8.0 Hz, 1H); 7.764 (d, J=8.0 Hz, 1H); 7.863 (d, J=8.4 Hz, 2H); 8.016 (d, J=6.8 Hz, 1H); 8.244 (s, 1H); 8.370 (s, 1H); 8.482 (d, J=8.8 Hz, 1H); ESI MS: m/z=510.4 [M++1]

Compound 6: 1H-NMR (400 MHz, CDCl3) δ=1.559 (s, 1H); 1.980 (s, 7H); 2.235 (m, 1H); 2.434 (m, 1H); 4.065 (s, 3H); 6.025 (s, 1H); 6.833 (d, J=8.4 Hz, 2H); 7.055 (d, J=7.6 Hz, 2H); 7.202 (s, 1H); 7.351 (m, 2H); 7.430 (t, J=7.2 Hz, 1H); 7.492 (t, J=7.2 Hz, 1H); 7.597 (t, J=7.6 Hz, 1H); 7.697 (d, J=8.0 Hz, 1H); 7.748 (d, J=8.4 Hz, 1H); 7.886 (d, J=9.6 Hz, 3H); 8.408 (s, 1H); 8.617 (d, J=8.0 Hz, 1H); 8.761 (s, 1H). ESI MS: m/z=510.4 [M++1]

EXAMPLE 20

Preparation of 1-(4-chlorophenyl)-2-(4-bromophenyl)-1-[2-(7-bromo-3-methoxy)naphthyl]-4-(N,N-dimethylamino)-butan-2-ol (Compounds 7 and 8)

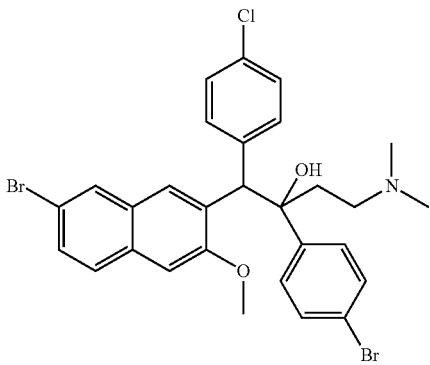 [SMILES: COc1cc2ccc(Br)cc2cc1C(c1ccc(Cl)cc1)C(O)(CCN(C)C)c1ccc(Br)cc1]

Compound 7 (A mesomer)
Compound 8 (B mesomer)

Using 6-bromo-2-methoxy-3-(4-chlorobenzyl)naphthalene to replace 2-benzyl-3-methoxynaphthalene, and 1-(4-bromophenyl)-3-(N,N-dimethylamino)-1-acetone to replace 1-(α-naphthyl)-3-(N,N-dimethylamino)-1-acetone, the procedures of Example 12 were repeated to obtain Compound 7 (mp: 219.5-220.4° C.) and Compound 8 (mp: 213.5-214.2° C.).

Compound 7: 1H-NMR (400 MHz, CDCl3) δ=1.567 (s, 1H); 2.049 (s, 8H); 2.226 (m, 1H); 3.698 (s, 1H); 4.898 (s, 1H); 6.751 (s, 1H); 7.256 (m, 4H); 7.367 (m, 4H); 7.649 (d, J=8.4 Hz, 2H); 7.843 (d, J=1.6 Hz, 1H); 8.163 (s, 1H); 8.348 (s, 1H).
ESI MS: m/z=618.3 [M++1]

Compound 8: 1H-NMR (400 MHz, CDCl3) δ=1.554 (s, 1H); 1.680 (m, 1H); 2.040 (s, 6H); 2.187 (m, 2H); 3.944 (s, 3H); 4.949 (s, 1H); 6.961 (d, J=8.4 Hz, 2H); 7.078 (s, 1H); 7.176 (d, J=8.4 Hz, 2H); 7.324 (d, J=8.8 Hz, 2H); 7.373 (d, J=9.2 Hz, 2H); 7.459 (dd, J1=2.0 Hz, J2=8.4 Hz, 1H); 7.571 (d, J=8.8 Hz, 1H); 7.960 (d, J=1.2 Hz, 1H); 8.204 (s, 1H); 8.624 (s, 1H).
ESI MS: m/z=618.3 [M++1]

EXAMPLE 21

Preparation of 1-phenyl-2-(4-bromophenyl)-1-[2-(7-bromo-3-methoxy)naphthyl]-4-(N,N-dimethylamino)-butan-2-ol (Compounds 9 and 10)

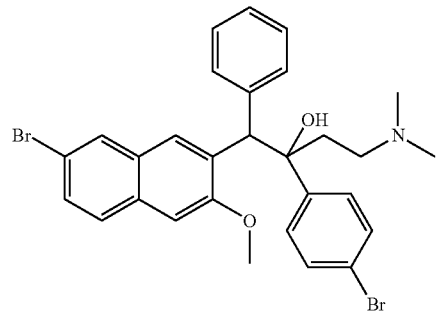 [SMILES: COc1cc2ccc(Br)cc2cc1C(c1ccccc1)C(O)(CCN(C)C)c1ccc(Br)cc1]

Compound 9 (A mesomer)
Compound 10 (B mesomer)

Using 6-bromo-2-methoxy-3-benzylnaphthalene to replace 2-benzyl-3-methoxynaphthalene, and 1-(4-bromophenyl)-3-(N,N-dimethylamino)-1-acetone to replace 1-(α-naphthyl)-3-(N,N-dimethylamino)-1-acetone, the procedures of Example 12 were repeated to obtain Compound 9 (mp: 189.8-190.7° C.) and Compound 10 (mp: 228.2-229.9° C.).

Compound 9: 1H-NMR (400 MHz, CDCl3) δ=1.560 (s, 1H); 1.698 (s, 1H); 2.036 (s, 6H); 2.193 (m, 2H); 3.951 (s, 3H); 4.996 (s, 1H); 6.991 (m, 3H); 7.077 (s, 1H); 7.232 (d, J=7.2 Hz, 2H); 7.344 (dd, J1=8.8 Hz, J2=12.0 Hz, 4H); 7.449 (dd, J1=2.0 Hz, J2=8.8 Hz, 1H); 7.567 (d, J=8.8 Hz, 1H); 7.964 (d, J=1.6 Hz, 1H); 8.147 (s, 1H); 8.669 (s, 1H).
ESI MS: m/z=584.2 [M++1]

Compound 10: 1H-NMR (400 MHz, CDCl3) δ=1.564 (m, 2H); 2.102 (m, 8H); 3.687 (s, 3H); 4.939 (s, 1H); 6.742 (s, 1H); 7.295 (m, 9H); 7.713 (d, J=6.8 Hz, 2H); 7.855 (d, J=1.6 Hz, 1H); 8.083 (s, 1H); 8.376 (s, 1H).
ESI MS: m/z=584.2 [M++1]

EXAMPLE 22

Preparation 1-phenyl-2-(3-bromophenyl)-1-[2-(7-bromo-3-methoxy)naphthyl]-4-(N,N-dimethylamino)-butan-2-ol (Compounds 11 and 12)

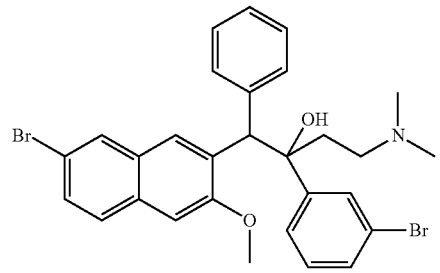 [SMILES: COc1cc2ccc(Br)cc2cc1C(c1ccccc1)C(O)(CCN(C)C)c1cccc(Br)c1]

Compound 11 (A mesomer)
Compound 12 (B mesomer)

Using 6-bromo-2-methoxy-3-benzylnaphthalene to replace 2-benzyl-3-methoxynaphthalene, and 1-(3-bromophenyl)-3-(N,N-dimethylamino)-1-acetone to replace 1-(α-naphthyl)-3-(N,N-dimethylamino)-1-acetone, the procedures of Example 12 were repeated to obtain Compound 11 (mp: 212.3-212.8° C.) and Compound 12 (mp: 200.2-200.6° C.).

Compound 11: 1H-NMR (400 MHz, CDCl3) δ=1.556 (s, 1H); 1.695 (d, J=6.8 Hz, 1H); 2.044 (s, 6H); 2.195 (m, 2H); 3.959 (s, 3H); 4.985 (s, 1H); 7.029 (m, 5H); 7.235 (d, J=7.6 Hz, 3H); 7.386 (d, J=7.6 Hz, 1H); 7.449 (dd, J1=1.6 Hz, J2=8.4 Hz, 1H); 7.567 (d, J=8.4 Hz, 1H); 7.600 (s, 1H); 7.965 (d, J=1.6 Hz, 1H); 8.197 (s, 1H); 8.673 (s, 1H).

ESI MS: m/z=584.3 [M++1]

Compound 12: 1H-NMR (400 MHz, CDCl3) δ=1.563 (m, 2H); 2.046 (m, 8H); 3.725 (s, 3H); 4.978 (s, 1H); 6.744 (s, 1H); 6.981 (t, J=8.0 Hz, 1H); 7.141 (d, J=7.6 Hz, 1H); 7.304 (m, 6H); 7.639 (s, 1H); 7.746 (m, 2H); 7.864 (d, J=1.6 Hz, 1H); 8.151 (s, 1H); 8.338 (s, 1H)

ESI MS: m/z=584.2 [M++1]

EXAMPLE 23

Preparation of 1-(4-chlorophenyl)-2-(2,4-difluorophenyl)-1-[2-(3-methoxy)naphthyl]-4-(N,N-dimethylamino)-butan-2-ol (Compounds 13 and 14)

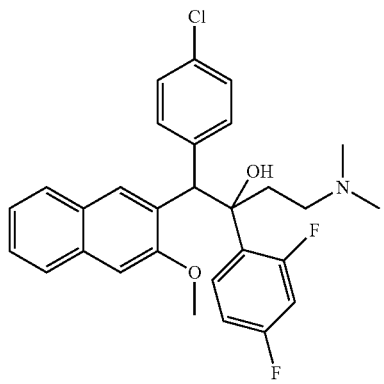 [SMILES: COc1cc2ccccc2cc1C(c1ccc(Cl)cc1)C(O)(CCN(C)C)c1ccc(F)cc1F]

Compound 13 (A mesomer)
Compound 14 (B mesomer)

Using 3-methoxy-2-(4-chlorobenzyl)naphthalene to replace 2-benzyl-3-methoxynaphthalene, and 1-(2,4-difluorophenyl)-3-(N,N-dimethylamino)-1-acetone to replace 1-(α-naphthyl)-3-(N,N-dimethylamino)-1-acetone, the procedures of Example 12 were repeated to obtain Compound 13 (oil) and Compound 14 (mp: 190.6-192.4° C.).

Compound 13 ESI MS: m/z=496.0 [M++1]

Compound 14: 1H-NMR (400 MHz, CDCl3) δ=2.139 (m, 10H); 3.943 (s, 3H); 5.293 (s, 1H); 6.736 (m, 2H); 6.964 (d, J=8.4 Hz, 2H); 7.116 (s, 1H); 7.254 (m, 2H); 7.328 (dt, J1=1.2 Hz, J2=6.8 Hz, 1H); 7.402 (dt, J1=1.2 Hz, J2=6.8 Hz, 1H); 7.508 (m, 1H); 7.702 (d, J=8.4 Hz, 1H); 7.824 (d, J=7.6 Hz, 2H); 8.434 (s, 1H); 8.756 (s, 1H).

ESI MS: m/z=496.3 [M++1]

EXAMPLE 24

Preparation of 1-(4-chlorophenyl)-2-(3-bromophenyl)-1-[2-(7-bromo-3-methoxy)naphthyl]-4-(N,N-dimethylamino)-butan-2-ol (Compounds 15 and 16)

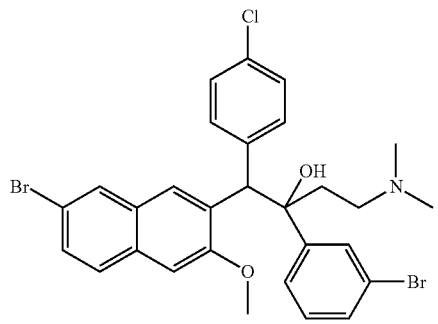 [SMILES: COc1cc2ccc(Br)cc2cc1C(c1ccc(Cl)cc1)C(O)(CCN(C)C)c1cccc(Br)c1]

Compound 15 (A mesomer)
Compound 16 (B mesomer)

Using 6-bromo-2-methoxy-3-(4-chlorobenzyl)naphthalene to replace 2-benzyl-3-methoxynaphthalene, and 1-(3-bromophenyl)-3-(N,N-dimethylamino)-1-acetone to replace 1-(α-naphthyl)-3-(N,N-dimethylamino)-1-acetone, the procedures of Example 12 were repeated to obtain Compound 15 (mp: 177.1-177.6° C.) and Compound 16 (mp: 183.9-184.9° C.).

Compound 15: 1H-NMR (400 MHz, CDCl3) δ=1.566 (m, 2H); 2.063 (m, 7H); 2.243 (m, 1H); 3.727 (s, 3H); 4.931 (s, 1H); 6.747 (s, 1H); 6984 (t, J=8.0 Hz, 1H); 7.140 (dd, J1=0.8 Hz, J2=8.0 Hz, 1H); 7.258 (d, J=8.8 Hz, 2H); 7.357 (m, 3H); 7.628 (s, 1H); 7.688 (d, J=8.4 Hz, 2H); 7.853 (d, J=1.6 Hz, 2H); 8.233 (s, 1H); 8.308 (s, 1H).

ESI MS: m/z=618.1 [M++1]

Compound 16: 1H-NMR (400 MHz, CDCl3) δ=1.659 (m, 2H); 2.104 (m, 8H); 3.956 (s, 3H); 4.952 (s, 1H); 6.967 (d, J=8.4 Hz, 2H); 7.110 (m, 2H); 7.189 (d, J=8.8 Hz, 2H); 7.276 (d, J=8.8 Hz, 1H); 7.384 (d, J=7.6 Hz, 1H); 7.460 (dd, J1=2.0 Hz, J2=8.4 Hz, 1H); 7.573 (d, J=8.8 Hz, 1H); 7.602 (s, 1H); 7.963 (d, J=1.6 Hz, 1H); 8.271 (s, 1H); 8.617 (s, 1H).

ESI MS: m/z=618.2 [M++1]

EXAMPLE 25

Preparation of 1-(4-chlorophenyl)-2-phenyl-1-[2-(7-bromo-3-methoxy)naphthyl]-4-(N,N-dimethylamino)-butan-2-ol (Compounds 17 and 18)

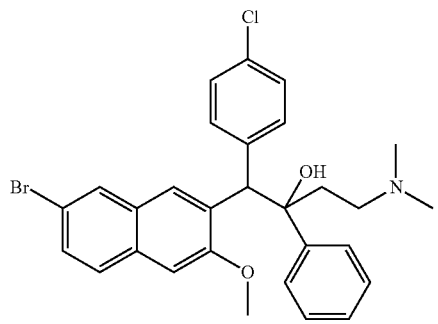 [SMILES: COc1cc2ccc(Br)cc2cc1C(c1ccc(Cl)cc1)C(O)(CCN(C)C)c1ccccc1]

Compound 17 (A mesomer)
Compound 18 (B mesomer)

Using 6-bromo-2-methoxy-3-(4-chlorobenzyl)naphthalene to replace 2-benzyl-3-methoxynaphthalene, and 1-phenyl-3-(N,N-dimethylamino)-1-acetone to replace 1-(α-naphthyl)-3-(N,N-dimethylamino)-1-acetone, the procedures of Example 12 were repeated to obtain Compound 17 (mp: 196.8-197.3° C.) and Compound 18 (mp: 182.2-182.8° C.).

Compound 17: 1H-NMR (400 MHz, CDCl3) δ=1.565 (m, 2H); 2.046 (m, 7H); 2.219 (m, 1H); 3.691 (s, 3H); 4.961 (s, 1H); 6.728 (s, 1H); 7.006 (t, J=7.2 Hz, 1H); 7.150 (t, J=7.6 Hz, 2H); 7.236 (s, 1H); 7.257 (s, 1H); 7.315 (dd, J1=2.0 Hz, J2=8.8 Hz, 1H); 7.364 (d, J=8.8 Hz, 1H); 7.485 (d, J=6.8 Hz, 2H); 7.651 (d, J=8.4 Hz, 2H); 7.842 (d, J=1.6 Hz, 1H); 8.062 (s, 1H); 8.383 (s, 1H).

ESI MS: m/z=540.2 [M++1]

Compound 18: 1H-NMR (400 MHz, CDCl3) δ=1.559 (s, 1H); 1.724 (d, J=10.0 Hz, 1H); 2.043 (s, 6H); 2.1875 (m, 2H); 3.947 (s, 3H); 5.020 (s, 1H); 6.932 (d, J=8.4 Hz, 2H); 7.082 (s, 1H); 7.147 (m, 3H); 7.255 (m, 2H); 7.451 (m, 3H); 7.576 (d, J=8.4 Hz, 1H); 7.969 (d, J=1.6 Hz, 1H); 8.137 (s, 1H); 8.681 (s, 1H).

ESI MS: m/z=540.2 [M++1]

EXAMPLE 26

Preparation of 1,2-diphenyl-1-[2-(7-bromo-3-methoxy)naphthyl]-4-(N,N-dimethylamino)-butan-2-ol (Compounds 19 and 20)

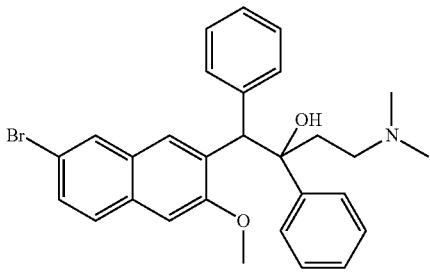 [SMILES: COc1cc2ccc(Br)cc2cc1C(c1ccccc1)C(O)(CCN(C)C)c1ccccc1]

Compound 19 (A mesomer)
Compound 20 (B mesomer)

Using 6-bromo-2-methoxy-3-benzylnaphthalene to replace 2-benzyl-3-methoxynaphthalene, and 1-phenyl-3-(N,N-dimethylamino)-1-acetone to replace 1-(α-naphthyl)-3-(N,N-dimethylamino)-1-acetone, the procedures of Example 12 were repeated to obtain Compound 19 (mp: 170.9-171.6° C.) and Compound 20 (mp: 201.9-203.7° C.).

Compound 19: 1H-NMR (400 MHz, CDCl3) δ=1.552 (s, 1H); 1.734 (d, J=10.8 Hz, 1H); 2.037 (s, 6H); 2.220 (m, 2H); 3.946 (s, 3H); 5.059 (s, 1H); 6.960 (m, 3H); 7.107 (m, 2H); 7.225 (m, 3H); 7.448 (m, 3H); 7.568 (d, J=8.8 Hz, 1H); 7.973 (d, 2 Hz, 1H); 8.078 (s, 1H); 8.733 (s, 1H).

ESI MS: m/z=504.3 [M++1]

Compound 20: 1H-NMR (400 MHz, CDCl3) δ=1.556 (s, 1H); 1.736 (d, J=10.8 Hz, 1H); 2.019 (s, 6H); 2.200 (m, 2H); 3.679 (s, 3H); 5.001 (s, 1H); 6.716 (s, 1H); 7.001 (t, J=7.2 Hz, 1H); 7.164 (m, 3H); 7.326 (m, 3H); 7.495 (d, J=8 Hz, 2H); 7.725 (d, J=7.2 Hz, 2H); 7.856 (d, 1.6 Hz, 1H); 8.001 (s, 1H); 8.424 (s, 1H).

ESI MS: m/z=504.3 [M++1]

EXAMPLE 27

Preparation of 1-(4-chlorophenyl)-2-(2-bromophenyl)-1-[2-(7-bromo-3-methoxy)naphthyl]-4-(N,N-dimethylamino)-butan-2-ol (Compounds 21 and 22)

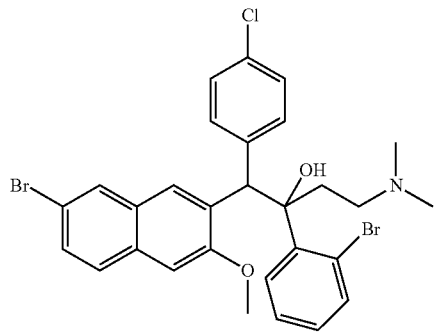 [SMILES: COc1cc2ccc(Br)cc2cc1C(c1ccc(Cl)cc1)C(O)(CCN(C)C)c1ccccc1Br]

Compound 21 (A mesomer)
Compound 22 (B mesomer)

Using 6-bromo-2-methoxy-3-(4-chlorobenzyl)naphthalene to replace 2-benzyl-3-methoxynaphthalene, and 1-(2-bromophenyl)-3-(N,N-dimethylamino)-1-acetone to replace 1-(α-naphthyl)-3-(N,N-dimethylamino)-1-acetone, the procedures of Example 12 were repeated to obtain Compound 21 (mp: 219.1-219.8° C.) and Compound 22 (mp: 180.8-181.6° C.).

Compound 21: 1 H-NMR (400 MHz, CDCl3) δ=1.568 (s, 1H); 2.022 (m, 9H); 3.664 (s, 3H); 5.889 (s, 1H); 6.728 (s, 1H); 6.885 (dt, J1=1.6 Hz, J2=6.8 Hz, 1H); 7.100 (dt, J1=1.2 Hz, J2=8.0 Hz, 1H); 7.264 (m, 2H); 7.371 (m, 3H); 7.684 (d, J=8.4 Hz, 2H); 7.836 (s, 1H); 7.984 (d, J=7.6 Hz, 1H); 8.296 (s, 1H).

ESI MS: m/z=618.3 [M++1]

Compound 22: 1 H-NMR (400 MHz, CDCl3) δ=1.569 (s, 1H); 2.024 (m, 8H); 2.738 (s, 1H); 3.966 (s, 3H); 6.080 (s, 1H); 6.975 (m, 3H); 7.085 (s, 1H); 7.163 (t, J=7.6 Hz, 1H); 7.285 (d, J=7.2 Hz, 2H); 7.454 (d, J=8.4 Hz, 1H); 7.556 (m, 2H); 7.825 (d, J=7.6 Hz, 1H); 7.971 (s, 1H); 8.359 (s, 1H); 8.632 (s, 1H).

ESI MS: m/z=618.5 [M++1]

EXAMPLE 28

Preparation of 1-phenyl-2-(2-bromophenyl)-1-[2-(7-bromo-3-methoxy)naphthyl]-4-(N,N-dimethylamino)-butan-2-ol (Compounds 23 and 24)

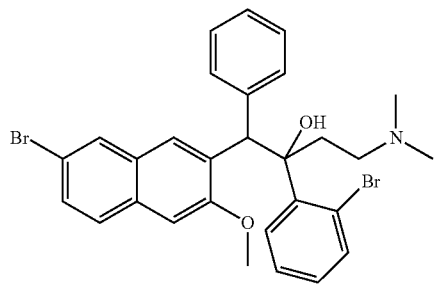 [SMILES: COc1cc2ccc(Br)cc2cc1C(c1ccccc1)C(O)(CCN(C)C)c1ccccc1Br]

Compound 23 (A mesomer)

Compound 24 (B mesomer)

Using 6-bromo-2-methoxy-3-benzylnaphthalene to replace 2-benzyl-3-methoxynaphthalene, and 1-(2-bromophenyl)-3-(N,N-dimethylamino)-1-acetone to replace 1-(α-naphthyl)-3-(N,N-dimethylamino)-1-acetone, the procedures of Example 12 were repeated to obtain Compound 23 (mp: 210.8-212.1° C.) and Compound 24 (mp: 200.2-200.7° C.).

Compound 23: 1 H-NMR (400 MHz, CDCl3) δ=1.569 (s, 1H); 2.095 (m, 8H); 2.816 (s, 1H); 3.641 (s, 3H); 5.900 (s, 1H); 6,710 (s, 1H); 6.878 (dt, J1=1.6 Hz, J2=7.6 Hz, 1H); 7.072 (dt, J1=1.2 Hz, J2=8.0 Hz, 1H); 7.206 (m, 1H); 7.323 (m, 4H); 7.428 (dd, J1=1.6 Hz, J2=8.0 Hz, 1H); 7.765 (d, J=7.6 Hz, 2H); 7.849 (d, J=1.2 Hz, 1H); 7.913 (d, J=7.2 Hz, 1H); 8.145 (s, 1H); 8.322 (s, 1H).

ESI MS: m/z=584.3 [M++1]

Compound 24: 1H-NMR (400 MHz, CDCl3) δ=2.097 (m, 9H); 2.746 (s, 1H); 3.969 (s, 3H); 6.090 (s, 1H); 7.031 (m, 6H); 7.455 (m, 5H); 7.810 (d, J=7.6 Hz, 1H); 7.980 (d, J=1.6 Hz, 1H); 8.294 (s, 1H); 8.695 (s, 1H).

ESI MS: m/z=584.0 [M++1]

EXAMPLE 29

Preparation of 1-phenyl-2-(1-naphthyl)-1-[2-(7-bromo-3-methoxy)naphthyl]-4-(N,N-dimethylamino)-butan-2-ol (Compounds 25 and 26)

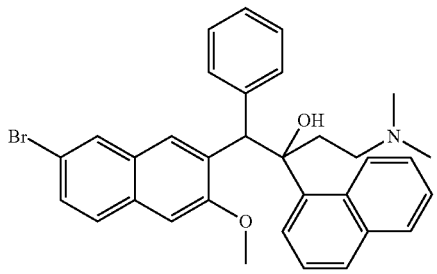 [SMILES: COc1cc2ccc(Br)cc2cc1C(c1ccccc1)C(O)(CCN(C)C)c1cccc2ccccc12]

Compound 25 (A mesomer)

Compound 26 (B mesomer)

Using 6-bromo-2-methoxy-3-benzylnaphthalene to replace 2-benzyl-3-methoxynaphthalene, the procedures of Example 12 were repeated to obtain Compound 25 (mp: 168.1-169.1° C.) and Compound 26 (mp: 200.9-201.6° C.).

Compound 25: 1H-NMR (400 MHz, CDCl3) δ=1.567 (s, 1H); 1.997 (s, 7H); 2.347 (s, 1H); 2.505 (s, 1H); 3.014 (s, 3H); 5.870 (s, 1H); 6.482 (s, 1H); 7.240 (m, 4H); 7.394 (m, 3H); 7.545 (m, 2H); 7.783 (d, J=8.0 Hz, 1H); 7.859 (s, 1H); 7.929 (m, 3H); 8.211 (s, 1H); 8.328 (s, 1H); 8.514 (d, J=8.4 Hz, 1H).

ESI MS: m/z=554.5 [M++1]

Compound 26: 1H-NMR (400 MHz, CDCl3) δ=1.562 (s, 1H); 1.920 (s, 1H); 1.983 (s, 6H); 2.177 (t, J=9.6 Hz, 1H); 2.449 (s, 1H); 4.065 (s, 3H); 6.045 (s, 1H); 6.881 (t, J=3.2 Hz, 3H); 7.105 (s, 2H); 7.156 (s, 1H); 7.320 (t, J=8.0 Hz, 1H); 7.487 (m, 2H); 7.602 (t, J=8.8 Hz, 2H); 7.679 (d, J=8.0 Hz, 1H); 7.892 (d, J=8.0 Hz, 1H); 8.027 (s, 1H); 8.337 (s, 1H); 8.641 (d, J=8.4 Hz, 1H); 8.753 (s, 1H).

ESI MS: m/z=554.5 [M++1]

EXAMPLE 30

Preparation of 1-(4-chlorophenyl)-2-(1-naphthyl)-1-[2-(3-methoxy)naphthyl]-4-(N,N-dimethylamino)-butan-2-ol hydrochloride (Compound 27)

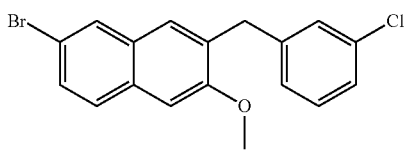 [SMILES: COc1cc2ccc(Br)cc2cc1Cc1cccc(Cl)c1]

In a 50 ml flask, 100 mg of Compound 6 (0.2 mmol) was dissolved in 5 ml of acetone, and 20 ml of hydrochloric acid ethyl ether solution was slowly added dropwise to the solution, sealed and stirred at room temperature for 3 h to precipitate a solid which was filtered, washed with acetone (5 ml*2), and dried to obtain a solid of 70 mg with a yield of 65.4% (mp: greater than 258° C.).

1H-NMR (400 MHz, DMSO-d6) δ=2.036 (s, 2H); 2.372 (s, 3H); 2.413 (s, 3H); 2.973 (s, 1H); 3.103 (s, 1H); 4.161 (s, 3H); 5.871 (s, 1H); 5.944 (s, 1H); 6.958 (d, J=8.4 Hz, 2H); 7.202 (d, J=7.6 Hz, 2H); 7.363 (m, 2H); 7.454 (m, 2H); 7.557 (t, J=6.8 Hz, 1H); 7.747 (d, J=8.0 Hz, 2H); 7.851 (m, 3H); 7.944 (d, J=8.4 Hz, 1H); 8.252 (s, 1H); 8.658 (d, J=8.0 Hz, 1H), 9.531 (s, 1H).

EXAMPLE 31

Preparation of 6-bromo-2-methoxy-3-(3-chlorobenzyl)-naphthalene

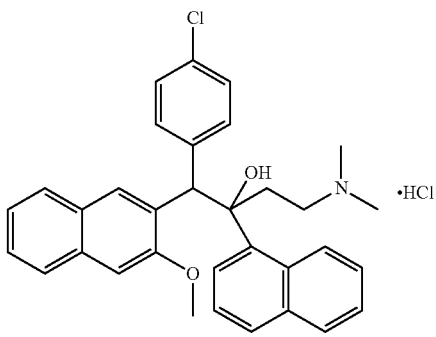 [SMILES: COc1cc2ccccc2cc1C(c1ccc(Cl)cc1)C(O)(CCN(C)C)c1cccc2ccccc12 ; Cl]

Using 3-chlorobromobenzene to replace bromobenzene, the procedures of Examples 6-7 were repeated to obtain the compound 2-methoxy-3-(3-chlorobenzyl)-6-bromonaphthalene.

EXAMPLE 32

Preparation of
6-bromo-2-methoxy-3-(4-methylbenzyl)-naphthalene

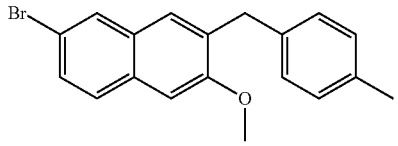 [SMILES: COc1cc2ccc(Br)cc2cc1Cc1ccc(C)cc1]

Using 4-bromotoluene to replace bromobenzene, the procedures of Examples 6-7 were repeated to obtain the compound 2-methoxy-3-(4-methylbenzyl)-6-bromonaphthalene.

EXAMPLE 33

Preparation of
6-bromo-2-methoxy-3-(3-methylbenzyl)-naphthalene

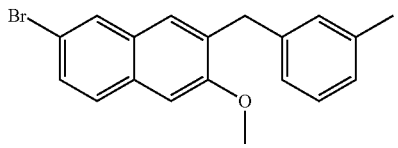 [SMILES: COc1cc2ccc(Br)cc2cc1Cc1cccc(C)c1]

Using 3-bromotoluene to replace bromobenzene, the procedures of Examples 6-7 were repeated to obtain the compound 2-methoxy-3-(3-methylbenzyl)-6-bromonaphthalene.

EXAMPLE 34

Preparation of
6-bromo-2-methoxy-3-(2-methylbenzyl)-naphthalene

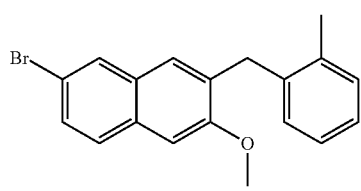 [SMILES: COc1cc2ccc(Br)cc2cc1Cc1ccccc1C]

Using 2-bromotoluene to replace bromobenzene, the procedures of Examples 6-7 were repeated to obtain the compound 2-methoxy-3-(2-methylbenzyl)-6-bromonaphthalene.

EXAMPLE 35

Preparation of
1,6-dibromo-2-methoxy-3-benzylnaphthalene and
1,6-dibromo-3-benzyl-2-naphthol

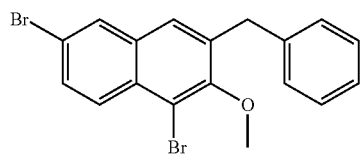

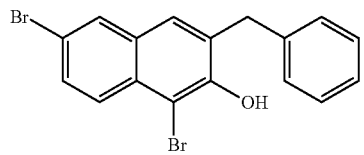

Using the Example 1 compound 4,7-dibromo-3-hydroxy-2-naphthoic acid as the starting material, the procedures of Examples 3-7 were repeated to obtain compounds 1,6-dibromo-2-methoxy-3-benzylnaphthalene and 1,6-dibromo-3-benzyl-2-naphthol.

EXAMPLE 36

Preparation of 1,6-dibromo-2methoxy-3-(4-methylbenzyl)-naphthalene and 1,6-dibromo-3-(4-methylbenzyl)-2-naphthol

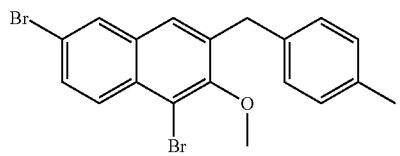

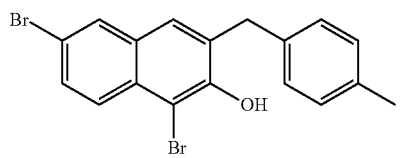

Using the Example 1 compound 4,7-dibromo-3-hydroxy-2-naphthoic acid as the starting material, and 4-bromotoluene to replace bromobenzene, the procedures of Examples 3-7 were repeated to obtain compounds 1,6-dibromo-2methoxy-3-benzylnaphthalene and 1,6-dibromo-3-benzyl-2-naphthol.

EXAMPLE 37

Preparation of 1,6-dibromo-2methoxy-3-(4-chlorobenzyl)-naphthalene and 1,6-dibromo-3-(4-chlorobenzyl)-2-naphthol

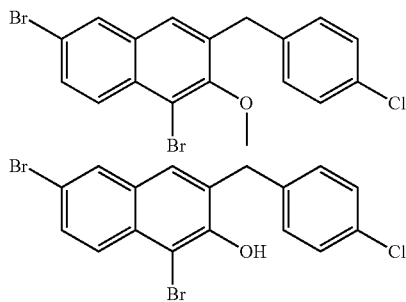

Using the Example 1 compound 4,7-dibromo-3-hydroxy-2-naphthoic acid as the starting material, and 4-chlorobromobenzene to replace bromobenzene, the procedures of Examples 3-7 were repeated to obtain compounds 1,6-dibromo-2methoxy-3-benzylnaphthalene and 1,6-dibromo-3-benzyl-2-naphthol.

EXAMPLE 38

Preparation of 1-(4-methylphenyl)-2-(1-naphthyl)-1-[2-(7-bromo-3-methoxy)naphthyl]-4-(N,N-dimethylamino)-butan-2-ol (Compounds 29 and 30)

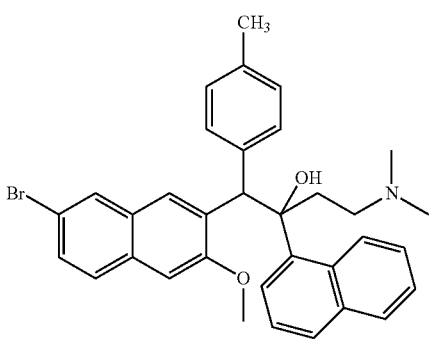 [SMILES: COc1cc2ccc(Br)cc2cc1C(c1ccc(C)cc1)C(O)(CCN(C)C)c1cccc2ccccc12]

Compound 29 (A mesomer)
Compound 30 (B mesomer)
Using 2-methoxy-3-(4-methylbenzyl)-6-bromonaphthalene to replace 2-benzyl-3-methoxynaphthalene, the procedures of Example 24 were repeated to obtain Compound 29 (oil) and Compound 30 (mp: 189.5-190.8° C.).

Compound 29: 1H-NMR (400 MHz, CDCl3): δ=1.900-2.190 (m, 12H), 2.546 (d, J=12.4 Hz, 1H), 4.058 (s, 3H), 6.022 (s, 1H), 6.688 (d, J=7.6 Hz, 2H), 7.005 (d, J=6.8 Hz, 2H), 7.141 (s, 1H), 7.315-7.366 (m, 1H), 7.446-7.497 (m, 2H), 7.585 (d, J=7.6 Hz, 2H), 7.678 (d, J=7.6 Hz, 1H), 7.879 (d, J=8.0 Hz, 1H), 7.924 (d, J=6.8 Hz, 1H), 8.008 (s, 1H), 7.628 (s, 1H), 8.646 (s, 1H). MS (ESI): [M+1]+=568.0.

Compound 30: 1H-NMR (400 MHz, DMSO-d6): δ=1.856-2.107 (m, 9H), 2.280 (s, 3H), 2.497 (m, 1H), 3.204 (s, 3H), 5.774 (s, 1H), 6.754 (s, 1H), 7.137 (d, J=8.0 Hz, 2H), 7.267-7.355 (m, 2H), 7.423-7.456 (m, 2H), 7.586 (d, J=8.0 Hz, 2H), 7.694 (d, J=7.6 Hz, 2H), 7.803 (d, J=7.6 Hz, 1H), 7.923 (s, 1H), 8.044 (d, J=7.2 Hz, 1H), 8.480 (s, 1H), 8.567 (d, J=8.4 Hz, 1H). MS (ESI): [M+1]+=568.1.

EXAMPLE 39

Preparation of 1-phenyl-2-(1-naphthyl)-1-[2-(4,7-dibromo-3-methoxy)naphthyl]-4-(N,N-dimethylamino)-butan-2-ol (Compounds 31 and 32)

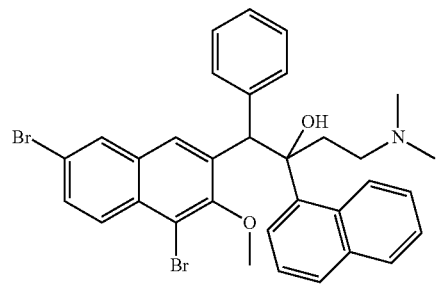 [SMILES: COc1c(C(c2ccccc2)C(O)(CCN(C)C)c2cccc3ccccc23)cc2cc(Br)ccc2c1Br]

Compound 31 (A mesomer)
Compound 32 (B mesomer)
Using 1,6-dibromo-2methoxy-3-benzylnaphthalene to replace 2-benzyl-3-methoxynaphthalene, the procedures of Example 24 were repeated to obtain Compound 31 (mp: 181.2-181.5° C.) and Compound 32 (mp: 189.9-190.5° C.).

Compound 31: 1H-NMR (400 MHz, CDCl3): δ=1.940-2.081 (m, 9H), 2.475 (m, 1H), 3.847 (s, 3H), 5.906 (s, 1H), 6.889-6.906 (m, 3H), 7.024-7.044 (m, 2H), 7.297 (t, J=8.0 Hz, 1H), 7.517 (t, J=7.6 Hz, 1H), 7.614-7.708 (m, 3H), 7.808 (d, J=7.2 Hz, 1H), 7.920 (d, J=8.4 Hz, 1H), 8.109 (d, J=9.2 Hz, 2H), 8.453 (br s, 1H), 8.639 (d, J=8.8 Hz, 1H), 8.959 (s, 1H). MS (ESI): [M+1]+=632.6.

Compound 32: 1H-NMR (400 MHz, CDCl3): δ=1.967-2.029 (m, 8H), 2.222 (m, 1H), 2.487 (m, 1H), 3.234 (s, 3H), 5.709 (s, 1H), 7.218-7.252 (m, 1H), 7.319-7.426 (m, 5H), 7.531-7.569 (m, 1H), 7.588 (d, J=8.0 Hz, 1H), 7.727-7.796 (m, 4H), 7.931 (d, J=1.6 Hz, 1H), 8.306 (d, J=7.2 Hz, 1H), 8.369 (br s, 1H), 8.510 (d, J=8.8 Hz, 1H), 8.805 (s, 1H). MS (ESI): [M+1]+=632.5.

EXAMPLE 40

Preparation of 1,6-dibromo-3-[1-phenyl 2-(1-naphthyl)-2-hydroxy-4-(N,N-dimethylamino)]butyl-2-naphthol (Compounds 33 and 34)

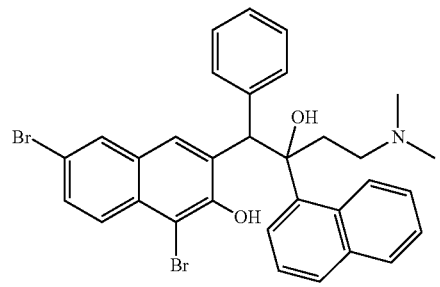 [SMILES: CN(C)CCC(O)(c1cccc2ccccc12)C(c1ccccc1)c1cc2cc(Br)ccc2c(Br)c1O]

Compound 33 (A mesomer)

Compound 34 (B mesomer)

Using 1,6-dibromo-3-benzyl-2-naphthol to replace 2-benzyl-3-methoxynaphthalene, the procedures of Example 24 were repeated to obtain Compound 33 (mp: 186.7-187.2° C.) and Compound 34 (mp: 185.8-186.4° C.).

Compound 33: 1H-NMR (400 MHz, CDCl3): δ=2.136 (m, 8H), 2.303-2.378 (m, 1H), 2.595 (d, J=12.8 Hz, 1H), 5.454 (s, 1H), 6.811-6.972 (m, 5H), 7.375 (t, J=8.0 Hz, 1H), 7.550-7.591 (m, 2H), 7.676 (t, J=7.6 Hz, 2H), 7.768-7.821 (m, 2H), 7.928 (s, 1H), 7.988 (d, J=8.0 Hz, 1H), 8.067 (d, J=9.2 Hz, 1H), 8.355 (d, J=7.2 Hz, 1H), 12.107 (br s, 1H). MS (ESI): [M+1]+=618.3.

Compound 34: 1H-NMR (400 MHz, CDCl3): δ=2.084-2.194 (m, 8H), 2.381 (m, 1H), 2.554 (m, 1H), 5.397 (s, 1H), 7.273-7.384 (m, 6H), 7.483 (t, J=7.6 Hz, 1H), 7.597-7.660 (m, 2H), 7.735 (d, J=8.8 Hz, 1H), 7.802-7.851 (m, 3H), 8.159 (d, J=7.2 Hz, 1H), 8.447 (d, J=8.8 Hz, 1H), 12.290 (br s, 1H). MS (ESI): [M+1]+=618.3.

EXAMPLE 41

Preparation of 1-(3-chlorophenyl)-2-(1-naphthyl)-1-[2-(7-bromo-3-methoxy)naphthyl]-4-(N,N-dimethylamino)-butan-2-ol (Compounds 35 and 36)

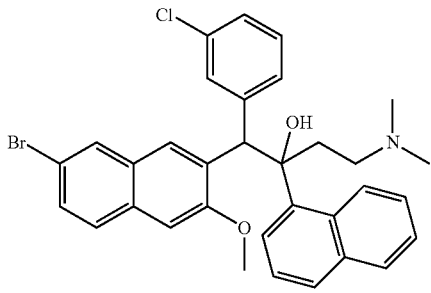

Compound 35 (A mesomer)

Compound 36 (B mesomer)

Using 2-methoxy-3-(3-chlorobenzyl)-6-bromonaphthalene to replace 2-benzyl-3-methoxynaphthalene, the procedures of Example 24 were repeated to obtain Compound 35 (mp: 176.8-177.3° C.) and Compound 36 (mp: 194.7-195.1° C.).

Compound 35: 1H-NMR (400 MHz, CDCl3): δ=1.882-2.157 (m, 9H), 2.461 (d, J=14.4 Hz, 1H), 4.084 (s, 3H), 5.999 (s, 1H), 6.781 (t, J=8.0 Hz, 1H), 6.846 (d, J=8.0 Hz, 1H), 7.012 (d, J=7.6 Hz, 1H), 7.166 (s, 1H), 7.242 (s, 1H), 7.359 (t, J=8.0 Hz, 1H), 7.473-7.499 (m, 2H), 7.580 (d, J=7.6 Hz, 1H), 7.617 (d, J=8.4 Hz, 1H), 7.688 (d, J=8.0 Hz, 1H), 7.890 (d, J=8.0 Hz, 1H), 7.985 (d, J=7.6 Hz, 1H), 8.031 (d, J=1.2 Hz, 1H), 8.331 (br s, 1H), 8.603 (d, J=8.8 Hz, 1H), 8.629 (s, 1H). MS (ESI): [M+1]+=588.6.

Compound 36: 1H-NMR (400 MHz, CDCl3): δ=2.016 (m, 8H), 2.284 (m, 1H), 2.492 (d, J=14.0 Hz, 1H), 3.032 (s, 3H), 5.826 (s, 1H), 6.485 (s, 1H), 7.204-7.307 (m, 6H), 7.412 (d, J=7.6 Hz, 1H), 7.521-7.562 (m, 2H), 7.779 (d, J=8.0 Hz, 1H), 7.836 (d, J=7.6 Hz, 1H), 7.870 (s, 1H), 7.950 (d, J=7.6 Hz, 2H), 8.308 (s, 2H), 8.462 (d, J=8.4 Hz, 1H). MS (ESI): [M+1]+=588.5.

EXAMPLE 42

Preparation of 1-(3-methylphenyl)-2-(1-naphthyl)-1-[2-(7-bromo-3-methoxy)naphthyl]-4-(N,N-dimethylamino)-butan-2-ol (Compounds 37 and 38)

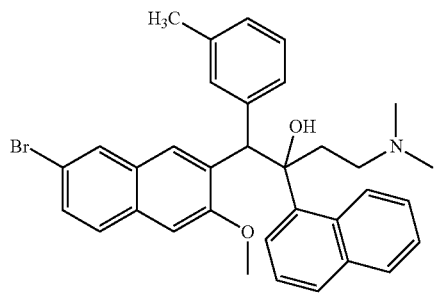 [SMILES: COc1cc2ccc(Br)cc2cc1C(c1cccc(C)c1)C(O)(CCN(C)C)c1cccc2ccccc12]

Compound 37 (A mesomer)

Compound 38 (B mesomer)

Using 2-methoxy-3-(3-methylbenzyl)-6-bromonaphthalene to replace 2-benzyl-3-methoxynaphthalene, the procedures of Example 24 were repeated to obtain Compound 37 (mp: 190.7-192.3° C.) and Compound 38 (mp: 185.6-186.9° C.).

Compound 37: 1H-NMR (400 MHz, CDCl3): δ=1.866-1.990 (m, 8H), 2.009 (s, 3H), 2.089-2.156 (m, 1H), 2.456 (d, J=14.4 Hz, 1H), 4.071 (s, 3H), 6.003 (s, 1H), 6.682 (d, J=7.2 Hz, 1H), 7.772 (t, J=7.6 Hz, 1H), 6.889 (s, 1H), 6.962 (d, J=7.6 Hz, 1H), 7.151 (s, 1H), 7.336 (t, J=7.6 Hz, 1H), 7.457-7.494 (m, 2H), 7.567-7.619 (m, 2H), 7.672 (d, J=8.0 Hz, 1H), 7.883 (d, J=8.0 Hz, 1H), 7.948 (d, J=7.2 Hz, 1H), 8.022 (s, 1H), 8.237 (br s, 1H), 7.646 (d, J=8.8 Hz, 1H), 8.692 (s, 1H). MS (ESI): [M+1]+=568.7.

Compound 38: 1H-NMR (400 MHz, CDCl3): δ=1.945-2.004 (m, 8H), 2.361-2.511 (m, 5H), 2.922 (s, 3H), 5.822 (s, 1H), 6.460 (s, 1H), 7.071 (d, J=7.6 Hz, 1H), 7.197 (t, J=7.6 Hz, 1H), 7.258-7.291 (m, 3H), 7.419 (t, J=7.2 Hz, 1H), 7.530-7.564 (m, 2H), 7.698 (s, 1H), 7.781-7.828 (m, 2H), 7.875-7.894 (m, 2H), 8.170 (br s, 1H), 8.298 (s, 1H), 8.519 (d, J=8.8 Hz, 1H). MS (ESI): [M+1]+=568.5.

EXAMPLE 43

Preparation of 1-(3-methylphenyl)-2-(1-naphthyl)-1-[2-(7-bromo-3-methoxy)naphthyl]-4-(N,N-dimethylamino)-butan-2-ol (Compounds 39 and 40)

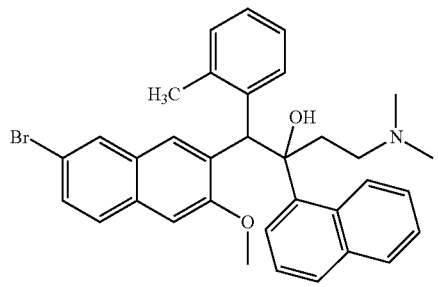 [SMILES: COc1cc2ccc(Br)cc2cc1C(c1ccccc1C)C(O)(CCN(C)C)c1cccc2ccccc12]

Compound 39 (A mesomer)

Compound 40 (B mesomer)

Using 2-methoxy-3-(2-methylbenzyl)-6-bromonaphthalene to replace 2-benzyl-3-methoxynaphthalene, the procedures of Example 24 were repeated to obtain Compound 39 (mp: 198.6-199.8° C.) and Compound 40 (mp: 207.8-208.1° C.).

Compound 39: 1H-NMR (400 MHz, CDCl3): δ=1.787 (s, 3H), 1.892-2.004 (m, 9H), 2.615 (d, J=9.6 Hz, 1H), 4.197 (s, 3H), 6.179 (s, 1H), 6.610 (d, J=7.2 Hz, 1H), 7.770 (t, J=7.6 Hz, 1H), 6.989 (t, J=7.2 Hz, 1H), 7.188 (s, 1H), 7.366-7.454 (m, 3H), 7.540 (dt, J=1.6, 7.2 Hz, 1H), 7.614 (t, J=8.0 Hz, 2H), 7.808 (d, J=7.2 Hz, 1H), 7.926 (d, J=1.6 Hz, 1H), 8.119 (s, 1H), 8.203 (br s, 1H), 8.222 (d, J=6.4 Hz, 1H), 8.466 (d, J=7.6 Hz, 1H), 8.741 (d, J=9.2 Hz, 1H). MS (ESI): [M+1]+= 568.7.

Compound 40: 1H-NMR (400 MHz, CDCl3): δ=2.006-2.048 (m, 8H), 2.399-2.589 (m, 5H), 2.875 (s, 3H), 6.104 (s, 1H), 6.458 (s, 1H), 7.128-7.231 (m, 3H), 7.277-7.293 (m, 3H), 7.425 (t, J=7.6 Hz, 1H), 7.517-7.588 (m, 2H), 7.816 (d, J=7.2 Hz, 1H), 7.856-7.888 (m, 2H), 8.202 (br s, 1H), 8.237 (s, 1H), 8.489-8.539 (m, 2H). MS (ESI): [M+1]+=568.6.

EXAMPLE 44

Determination of the Minimal Inhibitory Concentration (MIC) of the Compounds Against Standard Strain H37Rv of *mycobacterium tuberculosis* by using the Microplate Alamar Blue Assay (MABA)

Method: A sterile 96-well plate (Falcon3072; Becton Dickinson, Lincoln Park, N.J.) was used. The tested compound was dissolved in dimethylsulfoxide to obtain a primary solution with a concentration of 5 mg/ml. The wells for the highest concentration were added with 199 μl of 7H9 culture medium, 1 μl primary solution of the compound, and after being mixed to be homogeneous, the mixture was diluted twice in the other wells sequentially, so that the final compound concentrations were: 12.5, 6.25, 3.125, 1.56, 0.78, 0.39, 0.2, 0.1, 0.05, 0.025, 0.0125 μg/ml. The culture obtained by culturing *mycobacterium tuberculosis* H37RV for 2-3 weeks was selected to prepare a bacterial suspension, inoculated to the 7H9 culture medium containing 0.05% Tween 80, 10% ADC, statically cultivated at 37° C. for 1-2 weeks, grew until turbidity was McFarland 1 (equivalent to 107 CFU/ml), diluted in 1:20, added to each well in an amount of 100 μl, and the final concentration of bacterial solution was 106 CFU/ml. On each plate, 2 wells free of antibacterial drug were set as growth control wells, and the 96-well plate was incubated at 37° C. After 7 days, 50 μl of a mixture solution of 20 μl 10× Alamar Blue (product of Setotec Company) and 5% Tween 80 was added to the growth control wells, incubated at 37° C. for 24 h, if the color changed from blue to pink, the wells for various tested drugs were added with the above amount of the mixture solution of Alamar Blue and Tween 80, incubated at 37° C. for 24 h, and the colors of the wells were recorded, where MIC was defined as the minimal drug concentration capable of preventing the color change (from blue to pink).

Results: The minimal inhibitory concentrations (MIC) as determined by the MABA are shown in Table 1.

TABLE 1

The minimal inhibitory concentrations (MIC) as determined by the MABA

| Compound | MIC (μg/ml) |
|---|---|
| 1 | 2.047 |
| 2 | 3.178 |
| 3 | 2.883 |
| 4 | 0.244 |
| 5 | 3.052 |
| 6 | 1.454 |
| 7 | 1.000 |
| 8 | 0.956 |
| 9 | 0.118 |
| 10 | 2.000 |
| 11 | 0.103 |
| 12 | 1.000 |
| 13 | 1.000 |
| 14 | 0.754 |
| 15 | 2.166 |
| 16 | 0.184 |
| 17 | 2.000 |
| 18 | 0.109 |
| 19 | 0.206 |
| 20 | 2.000 |
| 21 | 2.000 |
| 22 | 0.111 |
| 23 | >32 |
| 24 | 0.224 |
| 25 | 0.594 |
| 26 | 1.977 |
| 27 | 0.962 |
| 29 | 0.222 |
| 30 | 1.000 |
| 31 | 0.124 |
| 32 | 1.000 |
| 33 | 1.000 |
| 34 | 4.000 |
| 35 | 0.114 |
| 36 | 3.773 |
| 37 | 0.180 |
| 38 | 8.000 |
| 37 | 0.258 |
| 38 | 1.999 |

EXAMPLE 45

Determination of the Minimal Inhibitory Concentration (MIC) of the Compounds Against Clinical Drug-Resistant Strains of *mycobacterium tuberculosis* by Using the Microplate Alamar Blue Assay (MABA)

The procedures were identical to those of Example 44. The clinical drug-resistant stains were 040 (resistant to isoniazid, rifampicin, protionamide, rifapentine, ofloxacin and oxcin) and 004 (resistant to streptomycin, rifampicin, rifapentine, ofloxacin and kanamycin).

Results: The minimal inhibitory concentrations (MIC) as determined by the MABA are shown in Table 2.

TABLE 2

The minimal inhibitory concentrations (MIC) of the compounds against various clinically isolated multiple drug-resistant mycobacterium tuberculosis as determined by the MABA

| Compound | MIC (μg/ml) M.tb stains (drug-resistant strains) | |
|---|---|---|
| | 40 | 004 |
| 35 | 0.125 | 0.5 |
| 37 | 0.125 | 0.5 |

Note: 040 (resistant to isoniazid, rifampicin, protionamide, rifapentine, ofloxacin and oxcin) and 004 (resistant to streptomycin, rifampicin, rifapentine, ofloxacin and kanamycin).

EXAMPLE 46

Experiments on the Acute Toxicity of the Compounds

The acute toxicities of Compounds 4, 16 and 25 were in vivo evaluated preliminarily in mice. Animal: male BALB/C mice, 18-20 g/mouse, 3 mice for blank control group, and 5 mice for each of test groups.

Method: Suspensions of Compound 25: 49 mg/ml (depended on the total amount of the compound provided); Compounds 4 and 16: 50 mg/ml were prepared in 0.5% CMC to separately. Each mouse of the 3 groups was subjected to oral intragastric administration of 0.2 ml of drug, and the doses were separately as follows: Compound 25: 490 mg/kg; and Compounds 4 and 16: 500 mg/kg. The blank control was administered with water. The consciousness, behavior and death of mice were observed every day after administration until 7 days of administration, and the survived mice were dissected after 7 days to observe pathological changes of tissues.

Results:
1. None of the animals of the 3 groups died within 7 days after the single administration, and all animals had a good mental status and behaved normally.
2. The body weights of the animals of the groups after 7 days of single administration are shown in Table 3.
3. No changes in the size and shape of the important organs such as liver, spleen, lung, heart were observed during the dissection, and they are not significantly different from those of the blank group animals.

TABLE 3

The body weights of the mice in each of the groups after 7 days of single administration

| Group | Body weight (g) | Group | Body weight (g) |
|---|---|---|---|
| Compound 25 | 21.81 | Compound 16 | 21.99 |
| | 24.32 | | 23.26 |
| | 19.8 | | 22.24 |
| | 22.68 | | 19.40 |
| | 21.97 | | 20.05 |
| | 22.12 ± 1.63 | | 21.39 ± 1.61 |
| Compound 4 | 23.38 | The blank | 22.64 |
| | 20.67 | | 18.50 |
| | 23.77 | | 23.07 |
| | 23.67 | | 21.40 ± 2.52 |
| | 22.18 | | |
| | 22.73 ± 1.32 | | |

CONCLUSION

It was shown in the preliminary study of the acute toxicity in mice that no death nor abnormality of the animals was observed for Compound 25 at a single dose of 490 mg/kg; and Compounds 4 and 16 at a single dose of 500 mg/kg. The LD50 value of Compound 25 in mice was greater than or equal to 490 mg/kg; and the LD50 values of Compounds 4 and 16 in mice were greater than or equal to 500 mg/kg.

All documents as cited in the present application are incorporated into the text by reference, and when the meanings of these documents are different from those of the present invention, the expressions of the present invention should be used.

What is claimed is:
1. A compound of Formula I,

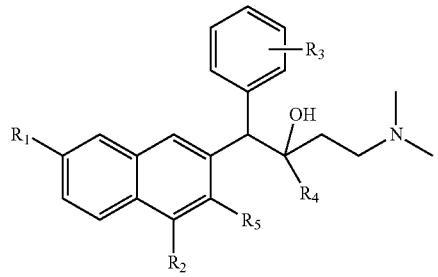

or an optical isomer, racemate, diastereomer, pharmaceutically acceptable salt, or solvate thereof, wherein
$R_1$ represents hydrogen, fluoro, chloro, bromo, iodo, hydroxy, an alkoxy, methoxy, nitro, amino, or an alkyl;
$R_2$ represents hydrogen, fluoro, chloro, bromo, iodo, an alkyl, nitro, or amino;
$R_3$ represents 1 to 5 substituents independently selected from the group consisting of hydrogen, fluoro, chloro, bromo, iodo, hydroxy, an alkoxy, methoxy, nitro, amino, and an alkyl;
$R_4$ represents phenyl, naphthyl or a heterocyclic group, wherein the phenyl, naphthyl, or heterocyclic group is optionally substituted with one or more substituents independently selected from the group consisting of fluoro, chloro, bromo, iodo, hydroxy, an alkoxy, methoxy, nitro, amino, and an alkyl; and
$R_5$ represents hydroxy, thiol, an alkoxy, an alkylthio, or a halogen.

2. The compound of Formula I according to claim 1, or an optical isomer, racemate, diastereomer, pharmaceutically acceptable salt, or solvate thereof, wherein
$R_1$ represents hydrogen, fluoro, chloro, bromo, iodo, or methoxy;
$R_2$ represents hydrogen, fluoro, chloro, bromo, or iodo;
$R_3$ represents hydrogen, fluoro, chloro, bromo, iodo, or a $C_{1-8}$ alkyl at an o-, m-, or p-position of the phenyl ring;
$R_4$ represents phenyl, substituted phenyl, or naphthyl; and
$R_5$ represents hydroxy, thiol, a $C_{1-8}$ alkoxy, or methylthio.

3. The compound of Formula I according to claim 2, or an optical isomer, racemate, diastereomer, pharmaceutically acceptable salt, or solvate thereof, wherein
$R_1$ represents hydrogen, fluoro, chloro, bromo, or iodo;
$R_3$ represents hydrogen, fluoro, chloro, bromo, iodo, or a $C_{1-6}$ alkyl at an o-, m-, or p-position of the phenyl ring;
$R_4$ represents phenyl, phenyl substituted with one or more halogens, or naphthyl; and
$R_5$ represents hydroxy or a $C_{1-6}$ alkoxy.

4. The compound of Formula I according to claim 3, or an optical isomer, racemate, diastereomer, pharmaceutically acceptable salt, or solvate thereof, wherein
$R_1$ represents hydrogen, chloro, or bromo;
$R_2$ represents hydrogen, chloro, or bromo;
$R_3$ represents hydrogen, chloro, bromo, or a $C_{1-4}$ alkyl at an o-, m-, or p-position of the phenyl ring;
$R_4$ represents phenyl, 2-bromophenyl, 3-bromophenyl, 4-bromophenyl, 2,4-difluorophenyl, 3,5-difluorophenyl, or naphthyl; and
$R_5$ represents hydroxy or a $C_{1-4}$ alkoxy.

5. The compound of Formula I according to claim 4, or an optical isomer, racemate, diastereomer, pharmaceutically acceptable salt, or solvate thereof, wherein $R_1$ represents hydrogen or bromo;
$R_2$ represents hydrogen or bromo;
$R_3$ represents hydrogen, chloro, bromo, or methyl substituted at an o-, m-, or p-position of the phenyl ring; and
$R_5$ represents hydroxy or methoxy.

6. A compound which is selected from the group consisting of 1-phenyl-2-(1-naphthyl)-1-[2-(3-methoxy)naphthyl]-4-(N,N-dimethylamino)-butan-2-ol,
1-(4-chlorophenyl)-2-(1-naphthyl)-1-[2-(7-bromo-3-methoxy)naphthyl]-4-(N,N-dimethylamino)-butan-2-ol,
1-(4-chlorophenyl)-2-(1-naphthyl)-1-[2-(3-methoxy)naphthyl]-4-(N,N-dimethylamino)-butan-2-ol,
1-(4-chlorophenyl)-2-(4-bromophenyl)-1-[2-(7-bromo-3-methoxy)naphthyl]-4-(N,N-dimethylamino)-butan-2-ol,
1-phenyl-2-(4-bromophenyl)-1-[2-(7-bromo-3-methoxy)naphthyl]-4-(N,N-dimethylamino)-butan-2-ol,
1-phenyl-2-(3-bromophenyl)-1-[2-(7-bromo-3-methoxy)naphthyl]-4-(N,N-dimethylamino)-butan-2-ol,
1-(4-chlorophenyl)-2-(2,4-difluorophenyl)-1-[2-(3-methoxy)naphthyl]-4-(N,N-dimethylamino)-butan-2-ol,
1-(4-chlorophenyl)-2-(3-bromophenyl)-1-[2-(7-bromo-3-methoxy)naphthyl]-4-(N,N-dimethylamino)-butan-2-ol,
1-(4-chlorophenyl)-2-phenyl-1-[2-(7-bromo-3-methoxy)naphthyl]-4-(N,N-dimethylamino)-butan-2-ol,
1,2-diphenyl-1-[2-(7-bromo-3-methoxy)naphthyl]-4-(N,N-dimethylamino)-butan-2-ol,
1-(4-chlorophenyl)-2-(2-bromophenyl)-1-[2-(7-bromo-3-methoxy)naphthyl]-4-(N,N-dimethylamino)-butan-2-ol,
1-phenyl-2-(2-bromophenyl)-1-[2-(7-bromo-3-methoxy)naphthyl]-4-(N,N-dimethylamino)-butan-2-ol,
1-phenyl-2-(1-naphthyl)-1-[2-(7-bromo-3-methoxy)naphthyl]-4-(N,N-dimethylamino)-butan-2-ol,
1-(4-methylphenyl)-2-(1-naphthyl)-1-[2-(7-bromo-3-methoxy)naphthyl]-4-(N,N-dimethylamino)-butan-2-ol,
1-phenyl-2-(1-naphthyl)-1-[2-(4,7-dibromo-3-methoxy)naphthyl]-4-(N,N-dimethylamino)-butan-2-ol,
1,6-dibromo-3-[1-phenyl-2-(1-naphthyl)-2-hydroxy-4-(N,N-dimethylamino)]butyl-2-naphthol,
1-(3-chlorophenyl)-2-(1-naphthyl)-1-[2-(7-bromo-3-methoxy)naphthyl]-4-(N,N-dimethylamino)-butan-2-ol,
1-(3-methylphenyl)-2-(1-naphthyl)-1-[2-(7-bromo-3-methoxy)naphthyl]-4-(N,N-dimethylamino)-butan-2-ol,
1-(2-methylphenyl)-2-(1-naphthyl)-1-[2-(7-bromo-3-methoxy)naphthyl]-4-(N,N-dimethylamino)-butan-2-ol, and
1-(4-chlorophenyl)-2-(1-naphthyl)-1-[2-(3-methoxy)naphthyl]-4-(N,N-dimethylamino)-butan-2-ol, or an optical isomer, racemate, diastereomer, pharmaceutically acceptable salt, or solvate thereof.

7. The compound according to claim 1, comprising a pharmaceutically acceptable salt of Formula I selected from the group consisting of a hydrochloride of Formula I, a hydrobromide of Formula I, a hydriodide of Formula I, and a sulfate of Formula I.

8. A process for preparing a compound according to claim 1, the process comprising the steps of:

subjecting a 4,7-substituted-3-hydroxy-2-naphthoic acid derivative of Formula II,

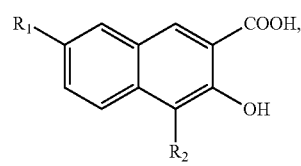

wherein $R_1$ and $R_2$ are as defined for the compound of Formula I in claim 1, to methylation by dimethyl sulfate to obtain a compound of Formula III,

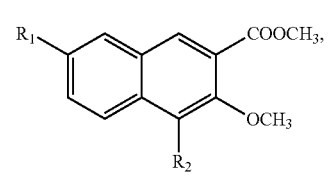

wherein $R_1$ and $R_2$ are as defined for the compound of Formula I in claim 1; subjecting the compound of Formula III to reduction by lithium aluminum hydride to obtain a compound of Formula IV,

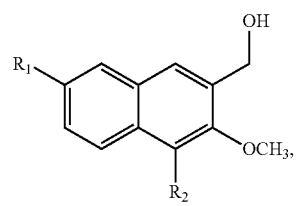

wherein $R_1$ and $R_2$ are as defined for the compound of Formula I in claim 1; subjecting the compound of Formula IV to oxidation by manganese dioxide to obtain a compound of Formula V,

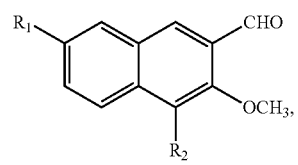

wherein $R_1$ and $R_2$ are as defined for the compound of Formula I in claim 1; subjecting the compound of Formula V to nucleophilic addition with a substituted bromobenzene of Formula VI in the presence of magnesium turnings,

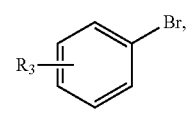

wherein $R_3$ is as defined for the compound of Formula I in claim 1, to obtain a compound of Formula VII,

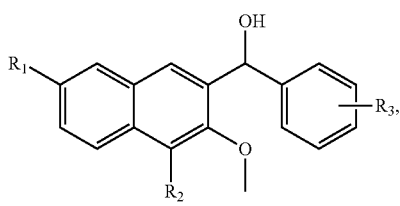

wherein $R_1$, $R_2$ and $R_3$ are as defined for the compound of Formula I in claim 1; subjecting the compound of Formula VII to reduction by a mixture of aluminum trichloride and sodium borohydride to obtain a compound of Formula VIII,

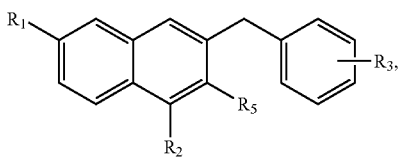

wherein $R_1$, $R_2$, $R_3$ and $R_5$ are as defined for the compound of Formula I in claim 1;
subjecting a substituted acetyl derivative of Formula IX,

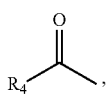

wherein $R_4$ is as defined for the compound of Formula I in claim 1,
to a Mannich reaction and then alkalization to obtain a compound of Formula X,

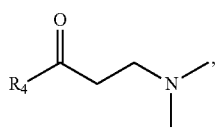

wherein $R_4$ is as defined for the compound of Formula I in claim 1;

and allowing a nucleophilic addition reaction between the compound of Formula VIII and the compound of Formula X to obtain a compound of Formula I,

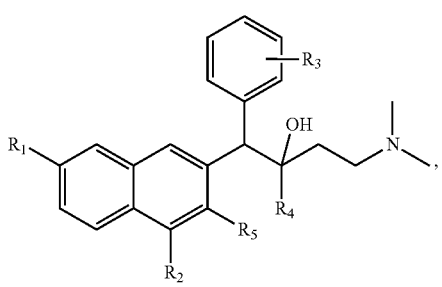

wherein $R_1$, $R_2$, $R_3$, $R_4$ and $R_5$ are as defined for the compound of Formula I in claim 1.

9. A pharmaceutical composition comprising a compound of claim 1 or an optical isomer, racemate, diastereomer, pharmaceutically acceptable salt, or solvate thereof, and one or more pharmaceutically acceptable carriers or excipients.

10. A method for the treatment and/or prophylaxis of a disease or disorder caused by a *tubercle bacillus* infection in a subject in need thereof, the method comprising administering to the subject a therapeutically and/or prophylactically effective amount of the pharmaceutical composition according to claim 9.

11. A method for the treatment and/or prophylaxis of a disease or disorder caused by a *tubercle bacillus* infection in a subject in need thereof, the method comprising administering to the subject a therapeutically and/or prophylactically effective amount of the compound according to claim 1 or an optical isomer, racemate, diastereomer, pharmaceutically acceptable salt, or solvate thereof.

* * * * *